(12) United States Patent
Kawarabayashi et al.

(10) Patent No.: US 11,413,387 B2
(45) Date of Patent: Aug. 16, 2022

(54) BLOOD PURIFICATION APPARATUS

(71) Applicant: Nikkiso Company Limited, Tokyo (JP)

(72) Inventors: Satoru Kawarabayashi, Shizuoka (JP); Sumiaki Matsuo, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 569 days.

(21) Appl. No.: 16/360,525

(22) Filed: Mar. 21, 2019

(65) Prior Publication Data

US 2019/0217001 A1 Jul. 18, 2019

Related U.S. Application Data

(63) Continuation of application No. PCT/JP2017/034309, filed on Sep. 22, 2017.

(30) Foreign Application Priority Data

Sep. 23, 2016 (JP) .............................. JP2016-186173

(51) Int. Cl.
*A61M 1/34* (2006.01)
*A61M 1/16* (2006.01)

(52) U.S. Cl.
CPC ............ *A61M 1/3403* (2014.02); *A61M 1/16* (2013.01); *A61M 1/3413* (2013.01);
(Continued)

(58) Field of Classification Search
CPC ...... A61M 1/16; A61M 1/165; A61M 1/1694; A61M 1/1696; A61M 1/3403;
(Continued)

(56) References Cited

U.S. PATENT DOCUMENTS

| 4,493,693 A | 1/1985 | Bilstad et al. |
| 5,336,051 A | 8/1994 | Tamari |

(Continued)

FOREIGN PATENT DOCUMENTS

| EP | 0330891 A1 | 9/1989 |
| EP | 2361643 A1 | 8/2011 |

(Continued)

OTHER PUBLICATIONS

Extended European Search Report for corresponding European Application No. 17853168.7 dated March 27, 2020.
(Continued)

*Primary Examiner* — Dirk R Bass
(74) *Attorney, Agent, or Firm* — Young Basile Hanlon & MacFarlane, P.C.

(57) ABSTRACT

There is provided a blood purification apparatus with which the efficiency of dialysate purification can be improved and the reduction in the amount of electrolytes contained in dialysate and necessary for treatment can be suppressed. The blood purification apparatus includes a storage device capable of storing a predetermined amount of dialysate that is necessary for blood purification treatment, a dialysate circulation line through which the dialysate is allowed to circulate by introducing the dialysate in the storage device into the dialyzer and draining waste liquid from the dialyzer into the storage device, and the dialysate purification device that purifies the dialysate in the dialysate circulation line. A treatment state in which the dialysate is allowed to be introduced into the dialyzer without flowing through the dialysate purification device and a purification state in which the dialysate is allowed to be purified by the dialysate purification device are taken switchably.

8 Claims, 15 Drawing Sheets

(52) U.S. Cl.
CPC ........ *A61M 1/3431* (2014.02); *A61M 1/3458* (2014.02); *A61M 2205/3337* (2013.01); *A61M 2205/3393* (2013.01)

(58) Field of Classification Search
CPC .............. A61M 1/3413; A61M 1/3431; A61M 1/3458; A61M 2205/3337; A61M 2205/3393
See application file for complete search history.

(56) References Cited

U.S. PATENT DOCUMENTS

| | | | |
|---|---|---|---|
| 5,920,054 | A | 7/1999 | Uber |
| 5,927,951 | A | 7/1999 | Tamari |
| 6,044,691 | A | 4/2000 | Kenley et al. |
| 6,374,084 | B1 | 4/2002 | Fok |
| 6,497,680 | B1 | 12/2002 | Holst |
| 6,868,720 | B2 | 3/2005 | Lobdell |
| 7,147,616 | B2 | 12/2006 | Pedrazzi et al. |
| 7,537,688 | B2 | 5/2009 | Tarumi et al. |
| 7,618,531 | B2 | 11/2009 | Sugioka et al. |
| 7,758,532 | B2 | 7/2010 | Mori et al. |
| 7,959,593 | B2 | 6/2011 | Ueda et al. |
| 8,011,905 | B2 | 9/2011 | Artsyukhivich |
| 8,092,414 | B2 | 1/2012 | Schnell et al. |
| 8,496,807 | B2 | 7/2013 | Mori et al. |
| 8,960,010 | B1 | 2/2015 | Crnkovich et al. |
| 9,192,708 | B2 | 11/2015 | Iwahori et al. |
| 9,662,433 | B2 | 5/2017 | Matsuo |
| 2003/0115965 | A1 | 6/2003 | Mittelstein et al. |
| 2004/0129616 | A1 | 7/2004 | Mori et al. |
| 2006/0043007 | A1 | 3/2006 | Tarumi et al. |
| 2006/0079826 | A1 | 4/2006 | Beden et al. |
| 2006/0226079 | A1 | 10/2006 | Mori et al. |
| 2006/0289342 | A1 | 12/2006 | Sugioka et al. |
| 2007/0108129 | A1 | 5/2007 | Mori et al. |
| 2009/0024070 | A1 | 1/2009 | Gelfand et al. |
| 2009/0043240 | A1 | 2/2009 | Robinson et al. |
| 2009/0312686 | A1 | 12/2009 | Sakamoto et al. |
| 2010/0168640 | A1 | 7/2010 | Kopperschmidt et al. |
| 2010/0234787 | A1 | 9/2010 | Masaoka |
| 2010/0274172 | A1 | 10/2010 | Guenther et al. |
| 2011/0089111 | A1 | 4/2011 | Mori et al. |
| 2011/0139690 | A1 | 6/2011 | Akita et al. |
| 2011/0213289 | A1 | 9/2011 | Toyoda |
| 2012/0000547 | A1 | 1/2012 | Gronau et al. |
| 2013/0035626 | A1 | 2/2013 | Suzuki |
| 2013/0118979 | A1 | 5/2013 | Kreymann et al. |
| 2013/0150766 | A1 | 6/2013 | Gambro |
| 2013/0150768 | A1 | 6/2013 | Sakamoto et al. |
| 2013/0172803 | A1 | 7/2013 | Gambro |
| 2013/0292313 | A1 | 11/2013 | Fava et al. |
| 2014/0138301 | A1 | 5/2014 | Iwahori et al. |
| 2014/0190876 | A1 | 7/2014 | Meyer et al. |
| 2014/0219829 | A1 | 8/2014 | Matsuo et al. |
| 2015/0021244 | A1 | 1/2015 | Furuhashi et al. |
| 2015/0150136 | A1 | 6/2015 | Furuhashi et al. |
| 2015/0238675 | A1 | 8/2015 | Carpani et al. |
| 2015/0238677 | A1 | 8/2015 | Akita et al. |
| 2016/0250405 | A1 | 9/2016 | Kogoshi et al. |
| 2017/0087291 | A1* | 3/2017 | Gerber ................. A61M 39/22 |
| 2017/0095602 | A1 | 4/2017 | Ishizaki et al. |
| 2017/0173249 | A1 | 6/2017 | Matsushita et al. |
| 2017/0312412 | A1 | 11/2017 | Mochizuki et al. |
| 2018/0071449 | A1 | 3/2018 | Hasegawa et al. |
| 2018/0080843 | A1 | 3/2018 | Funamura et al. |
| 2018/0140766 | A1 | 5/2018 | Mochizuki et al. |
| 2018/0228961 | A1 | 8/2018 | Takeuchi et al. |
| 2018/0318490 | A1 | 11/2018 | Naruse et al. |

FOREIGN PATENT DOCUMENTS

| | | |
|---|---|---|
| EP | 2535067 A1 | 12/2012 |
| EP | 2883558 A1 | 6/2015 |
| JP | S60-153138 U | 10/1985 |
| JP | S64-022357 U | 2/1989 |
| JP | H01-201263 A | 8/1989 |
| JP | H03-001290 | 1/1991 |
| JP | H03-073162 A | 3/1991 |
| JP | H03-099671 | 9/1991 |
| JP | H06-047090 B2 | 2/1994 |
| JP | H08-510812 A | 11/1996 |
| JP | 2002-113096 A | 4/2002 |
| JP | 2003-093501 A | 4/2003 |
| JP | 2003-093503 A | 4/2003 |
| JP | 2003-519539 A | 6/2003 |
| JP | 2003-265601 A | 9/2003 |
| JP | 2003-290342 A | 10/2003 |
| JP | 2004-016619 A | 1/2004 |
| JP | 2004-049493 | 2/2004 |
| JP | 2004-049494 A | 2/2004 |
| JP | 2006-006836 | 6/2004 |
| JP | 2004-187990 A | 7/2004 |
| JP | 2004-313522 A | 11/2004 |
| JP | 2005-253555 A | 9/2005 |
| JP | 2006-280775 A | 10/2006 |
| JP | 2007-007435 A | 1/2007 |
| JP | 3128724 U | 1/2007 |
| JP | 2007-020962 A | 2/2007 |
| JP | 2007-135885 A | 6/2007 |
| JP | 2007-167108 A | 7/2007 |
| JP | 2007-236924 | 9/2007 |
| JP | 2007-268257 | 10/2007 |
| JP | 2007-282737 A | 11/2007 |
| JP | 2008-289635 A | 12/2008 |
| JP | 2009-112651 A | 5/2009 |
| JP | 2009-131412 A | 6/2009 |
| JP | 2009-525770 A | 7/2009 |
| JP | 2009-207706 A | 9/2009 |
| JP | 2010-273784 A | 12/2009 |
| JP | 2010-000161 A | 1/2010 |
| JP | 2010-029376 | 2/2010 |
| JP | 2010-136841 A | 6/2010 |
| JP | 2010-184029 A | 8/2010 |
| JP | 2010-188170 A | 9/2010 |
| JP | 2010-273693 A | 12/2010 |
| JP | 2011-030880 A | 2/2011 |
| JP | 2011-161060 A | 8/2011 |
| JP | 2012-034782 A | 2/2012 |
| JP | 2012-095842 A | 5/2012 |
| JP | 2012-095843 A | 5/2012 |
| JP | 2012-139405 A | 7/2012 |
| JP | 2012-192099 A | 10/2012 |
| JP | 2012-192100 A | 10/2012 |
| JP | 2012-192101 A | 10/2012 |
| JP | 2012-200340 A | 10/2012 |
| JP | 2013-027494 A | 2/2013 |
| JP | 2013-027495 A | 2/2013 |
| JP | 2013-056079 A | 3/2013 |
| JP | 2014-097197 A | 5/2014 |
| JP | 2014-184108 A | 10/2014 |
| JP | 5699008 B2 | 4/2015 |
| WO | 94/28309 A1 | 12/1994 |
| WO | 2001/051106 A1 | 7/2001 |
| WO | 2004/000391 A1 | 12/2003 |
| WO | 2005/118485 A1 | 12/2005 |
| WO | 2007/073739 A1 | 7/2007 |
| WO | 2007/093064 A1 | 8/2007 |
| WO | 2009/004777 A1 | 1/2009 |
| WO | 2009/064741 A1 | 5/2009 |
| WO | 2009/071103 A1 | 6/2009 |
| WO | 2009/074588 A1 | 6/2009 |
| WO | 2010/020390 A1 | 2/2010 |
| WO | 2011/099521 A1 | 8/2011 |
| WO | 2012/017959 A1 | 2/2012 |
| WO | 2012/050781 A2 | 4/2012 |
| WO | 2013/031965 A1 | 3/2013 |
| WO | 2013/151114 A1 | 10/2013 |
| WO | 2014/024972 A1 | 2/2014 |
| WO | 2014/107656 A1 | 7/2014 |
| WO | 2015/068833 A1 | 5/2015 |

(56) References Cited

FOREIGN PATENT DOCUMENTS

WO      2015/162593 A1    10/2015
WO      2015/177606 A1    11/2015

OTHER PUBLICATIONS

International Search Report from the Japanese Patent Office for Application No. PCT/JP2017/002570 dated Feb. 28, 2017.
Co-pending U.S. Appl. No. 15/387,913 published as US2017/0095602A1 filed Dec. 22, 2016.
Co-pending U.S. Appl. No. 15/819,219 published as US2018/0071449A1 filed Nov. 21, 2017.
Co-pending U.S. Appl. No. 15/823,794 published as US2018/0080843A1 filed Nov. 28, 2017.
Co-pending U.S. Appl. No. 15/874,023 published as US2018/0140766A1 filed on Jan. 18, 2018.
Co-pending U.S. Appl. No. 15/952,419 filed, published as US2018/0228961 filed Aug. 16, 2018.
Potentially Related Co-pending U.S. Appl. No. 16/037,170, published as US2018/0318490A1 filed Nov. 8, 2018.
(Online), 2015, (search date Dec. 6, 2017), internet: <URL: http://yanhd.net/cgi-bin/c-board/c-board.cgi?cmd=ntr;tree=16897;id=hd>, non-official translation (Regarding Retransfusion and Reinfusion from ECUM with Personal Dialysis Apparatus).
Potentially Related Co-pending U.S. Appl. No. 16/296,679, filed Mar. 8, 2019.

* cited by examiner

[Fig. 1]
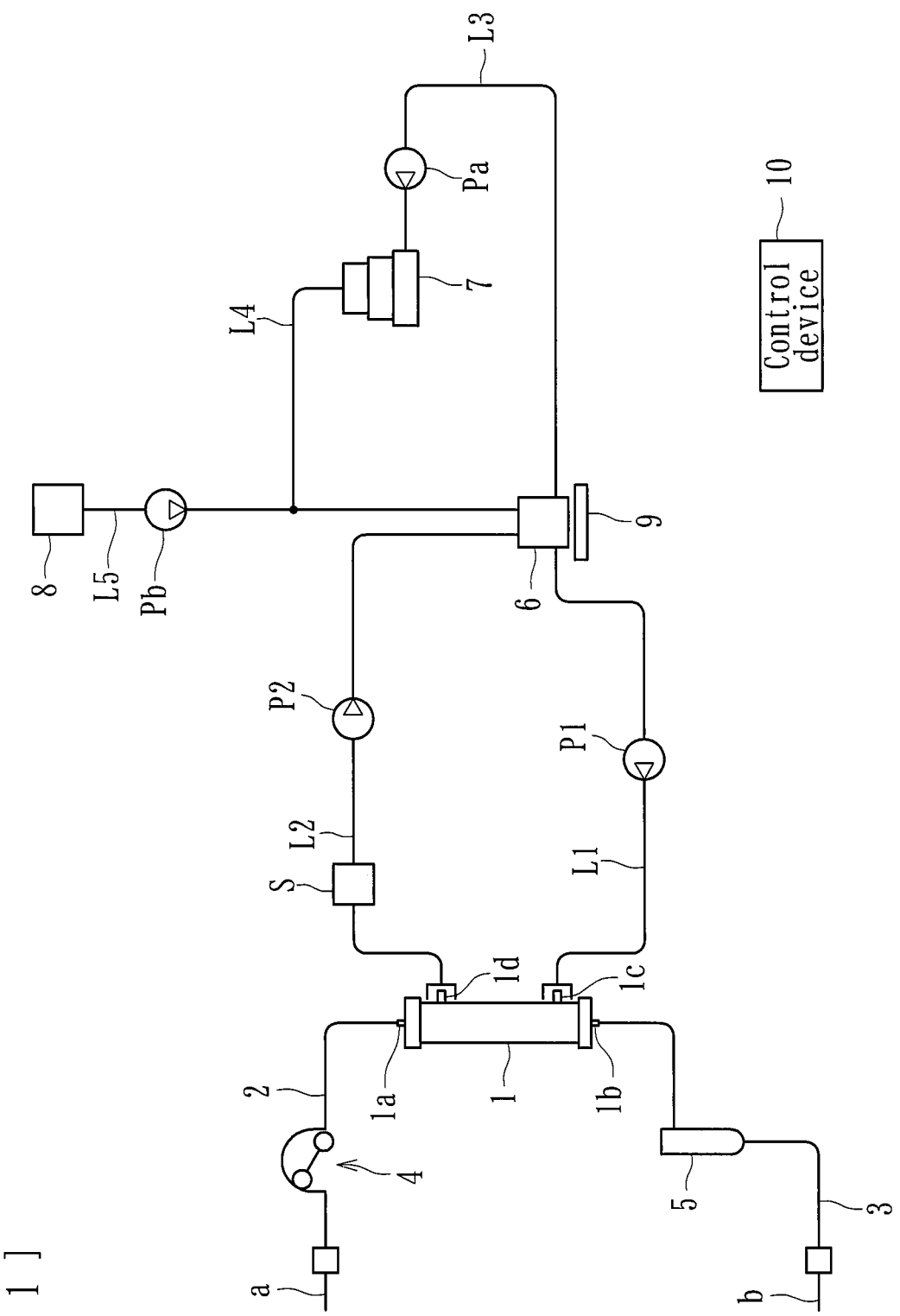

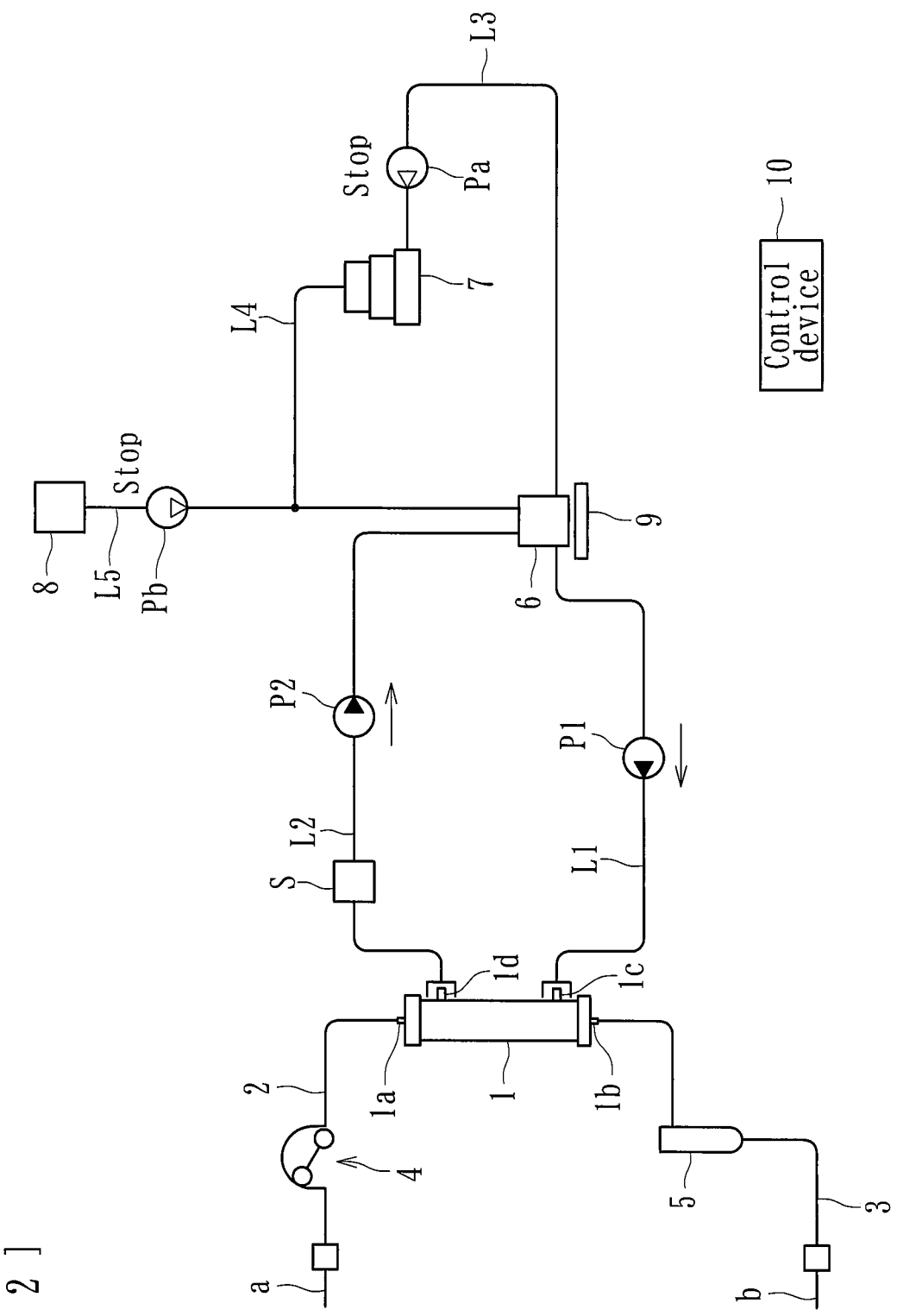
[Fig. 2]

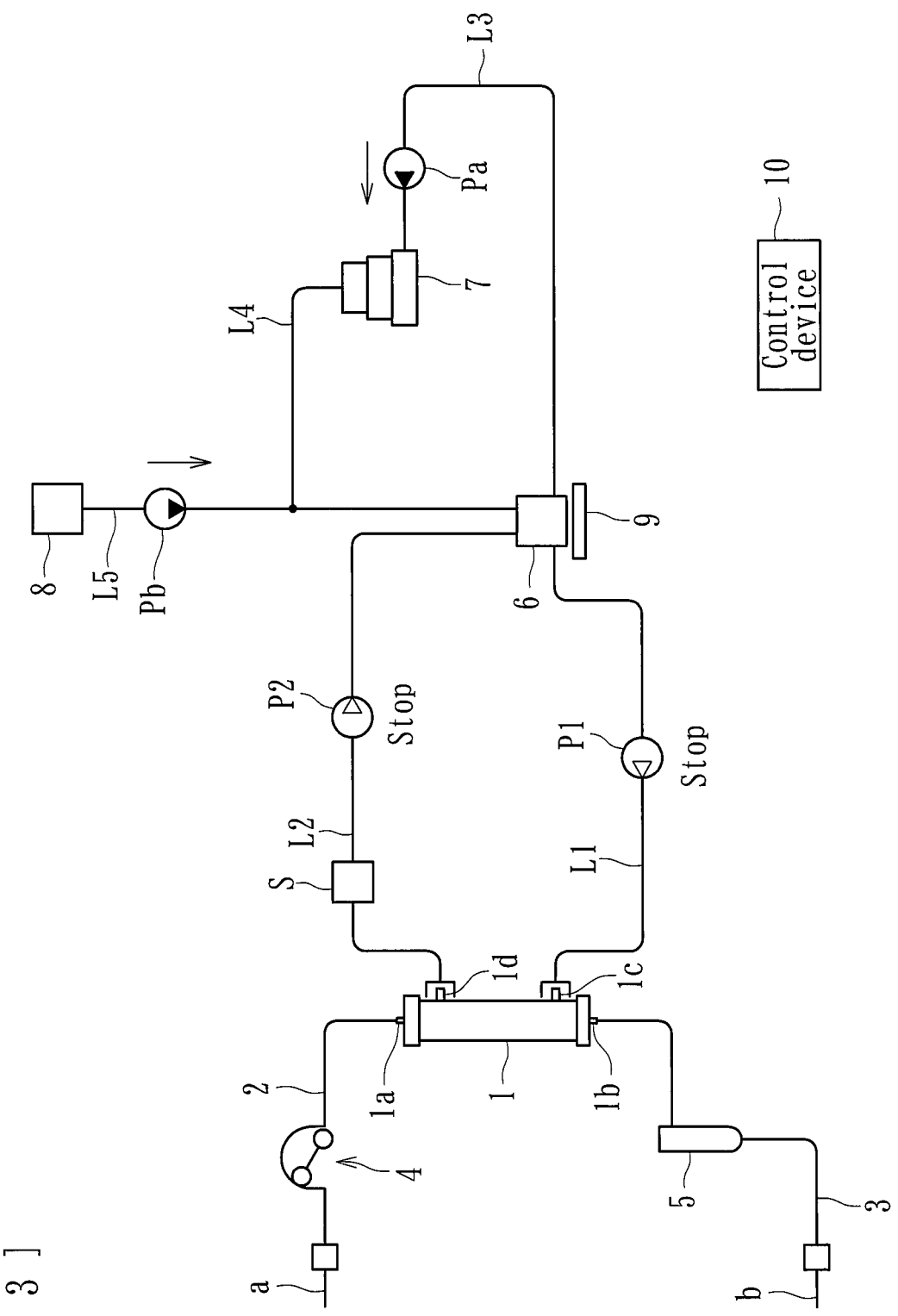
[Fig. 3]

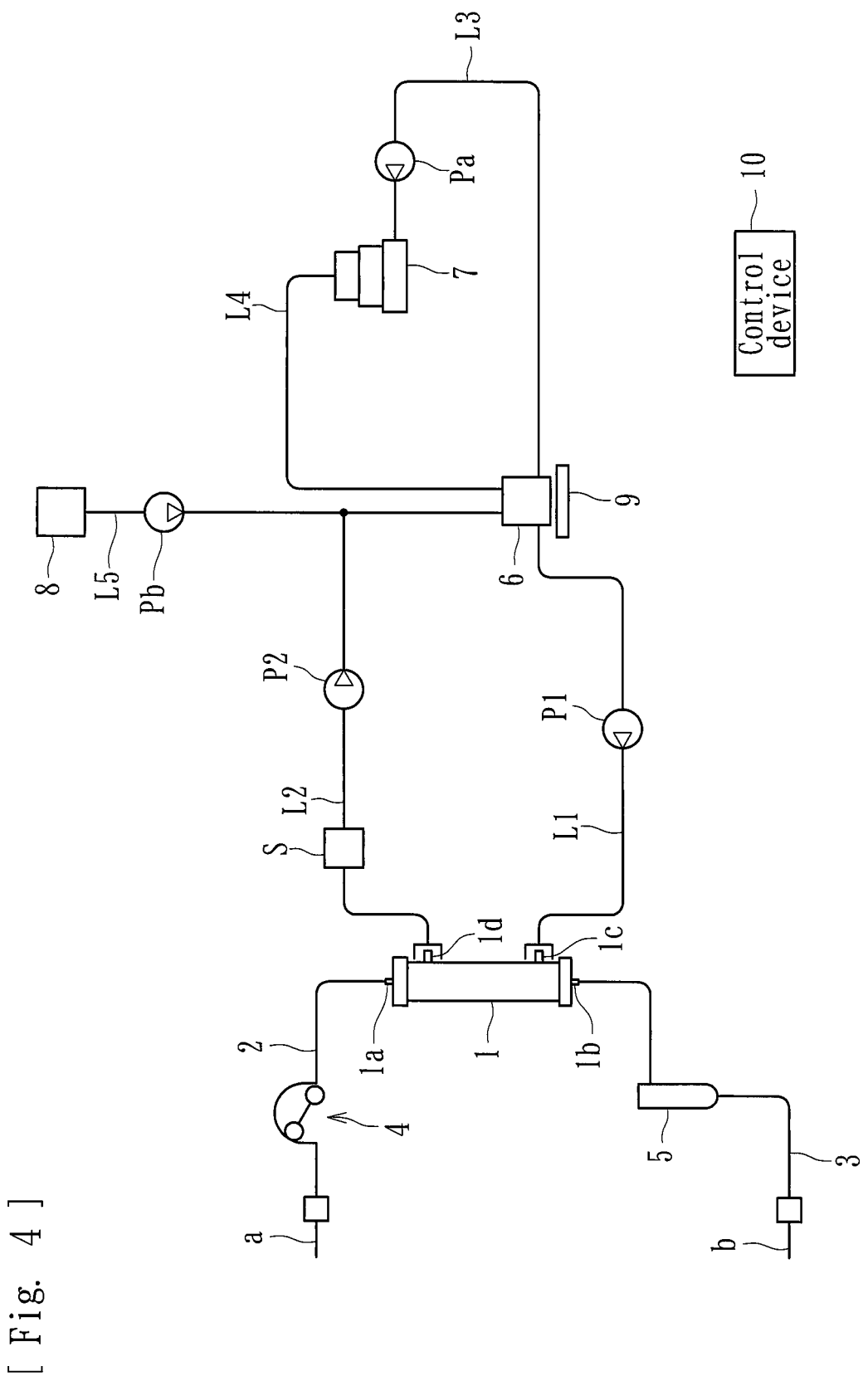
[Fig. 4]

[Fig. 5]
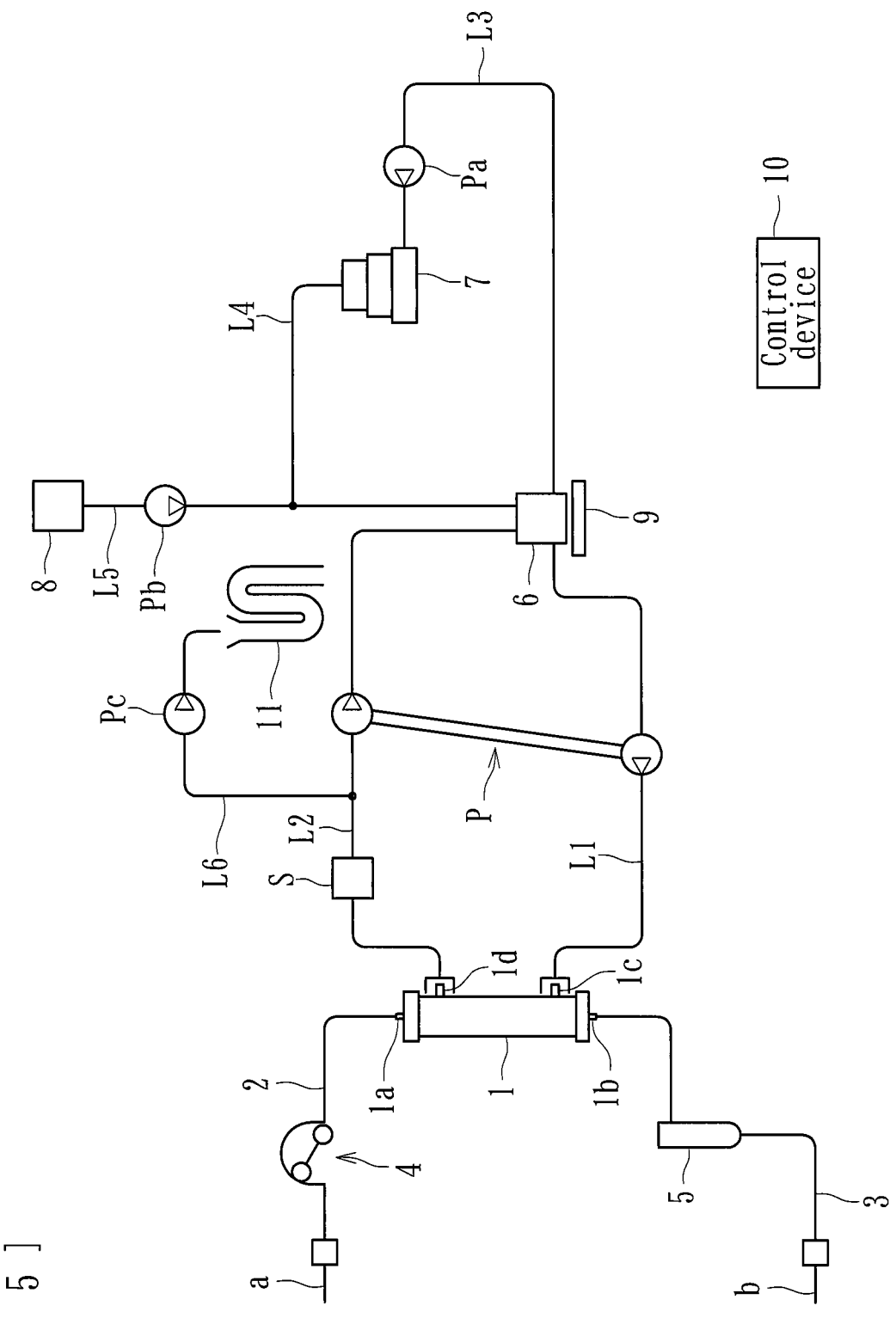

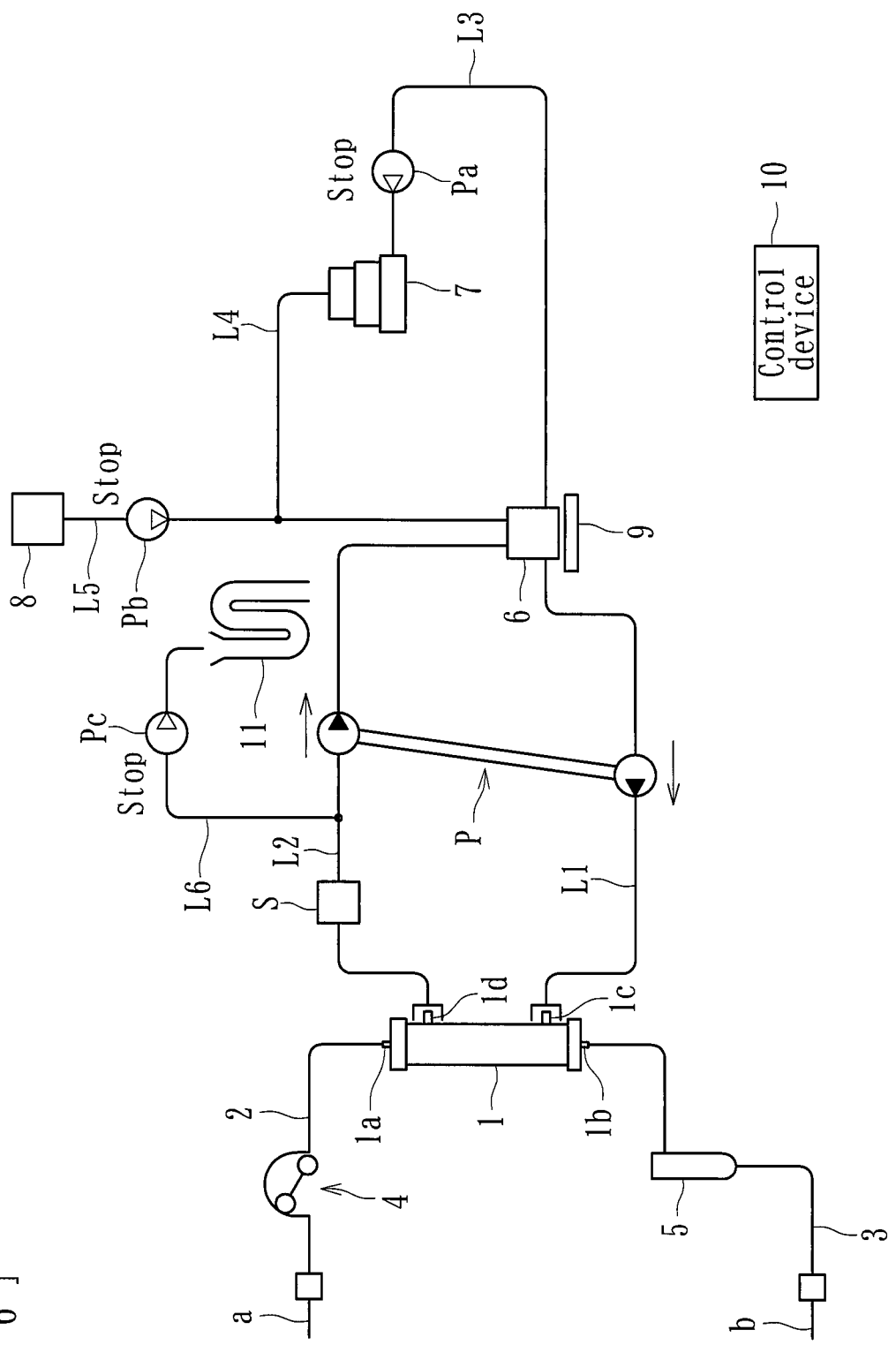
[Fig. 6]

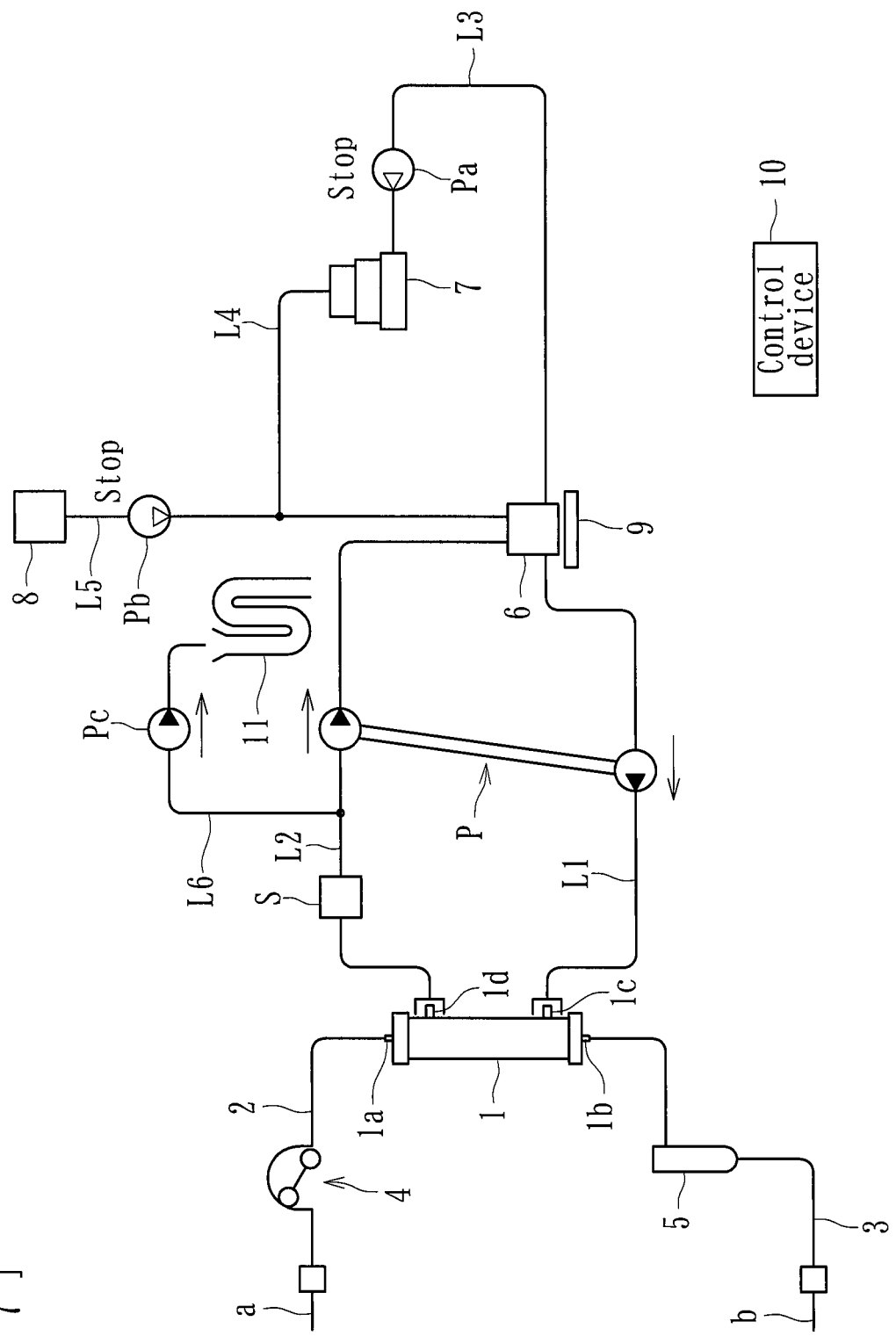
[Fig. 7]

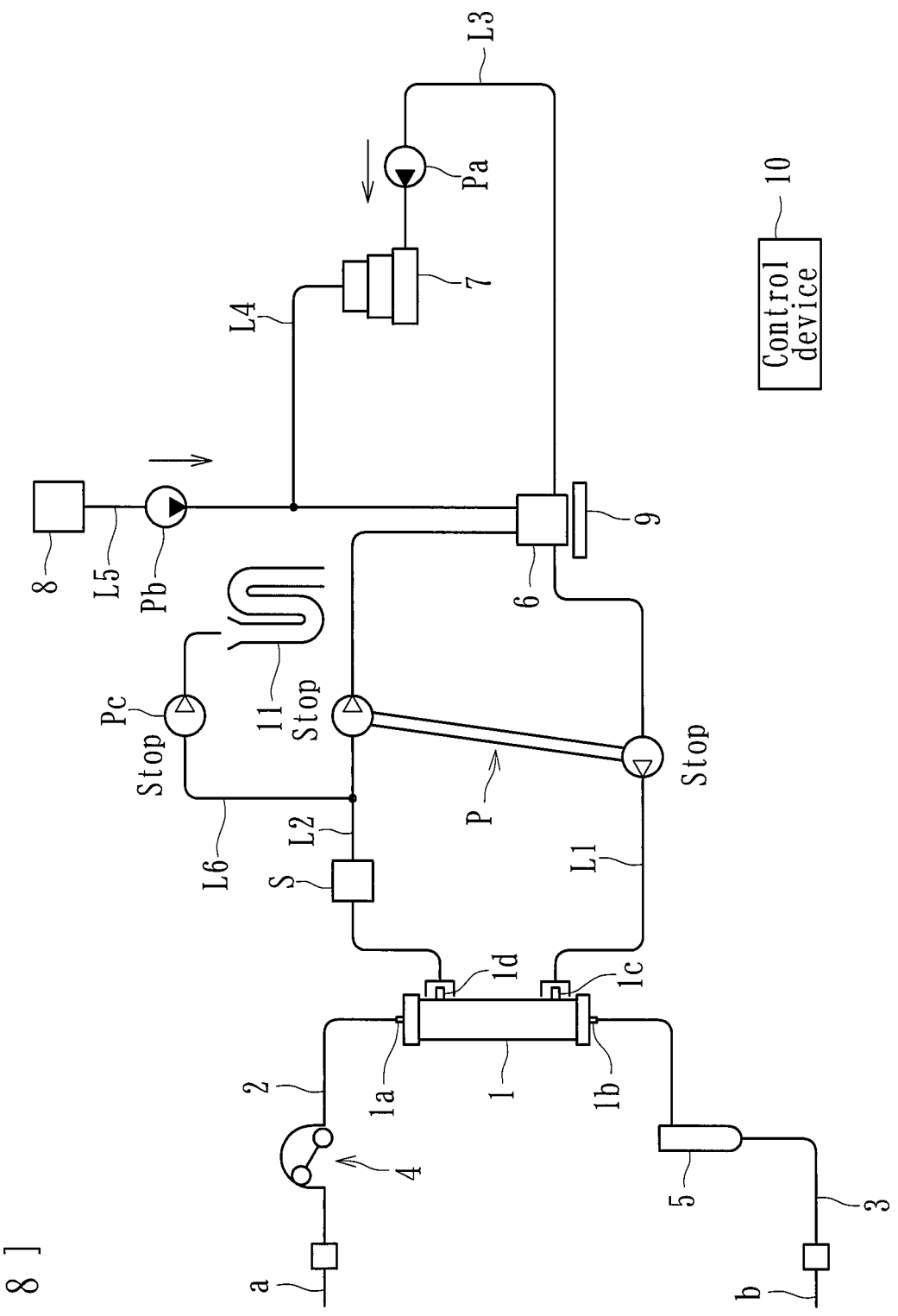
[Fig. 8]

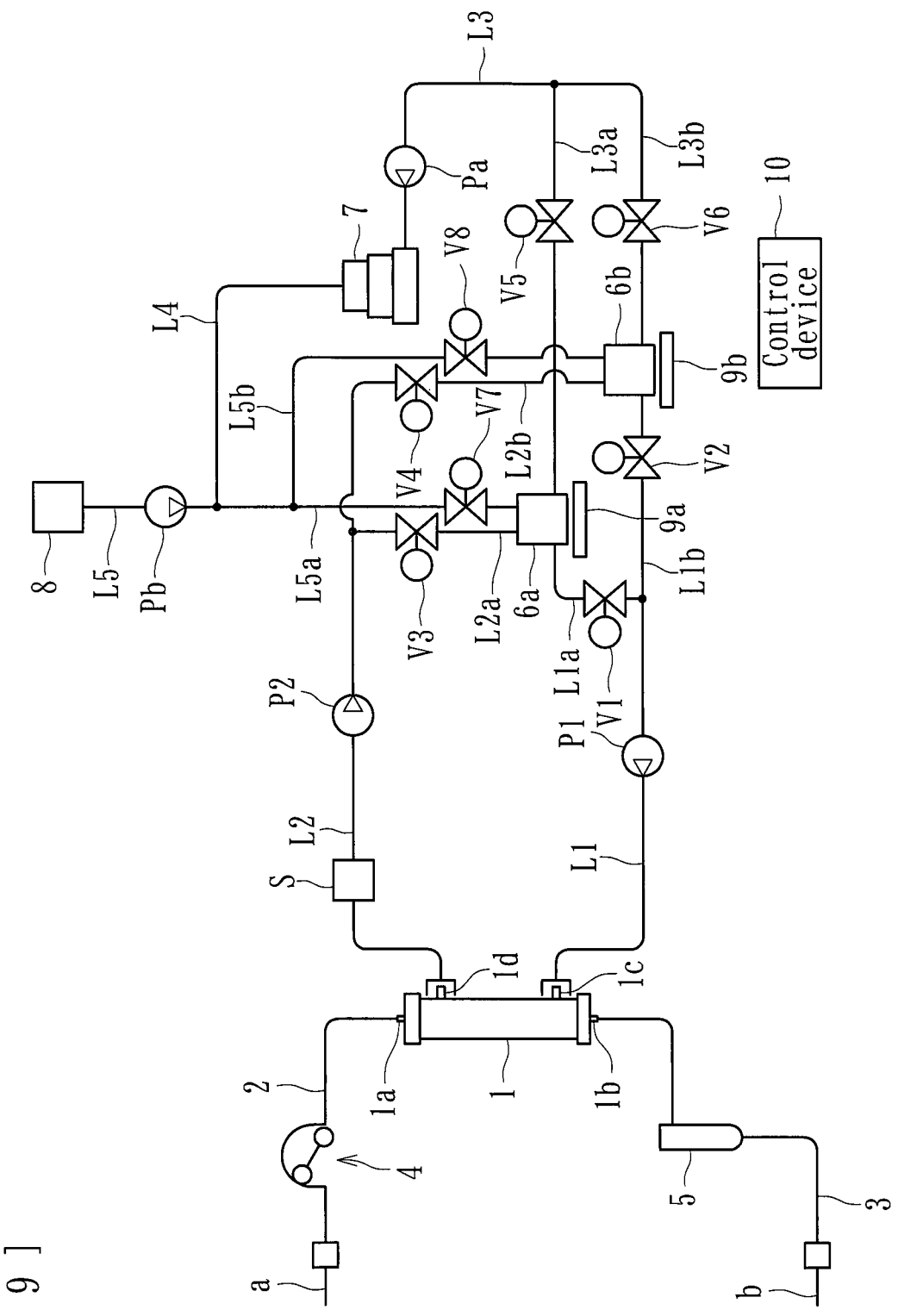
[Fig. 9]

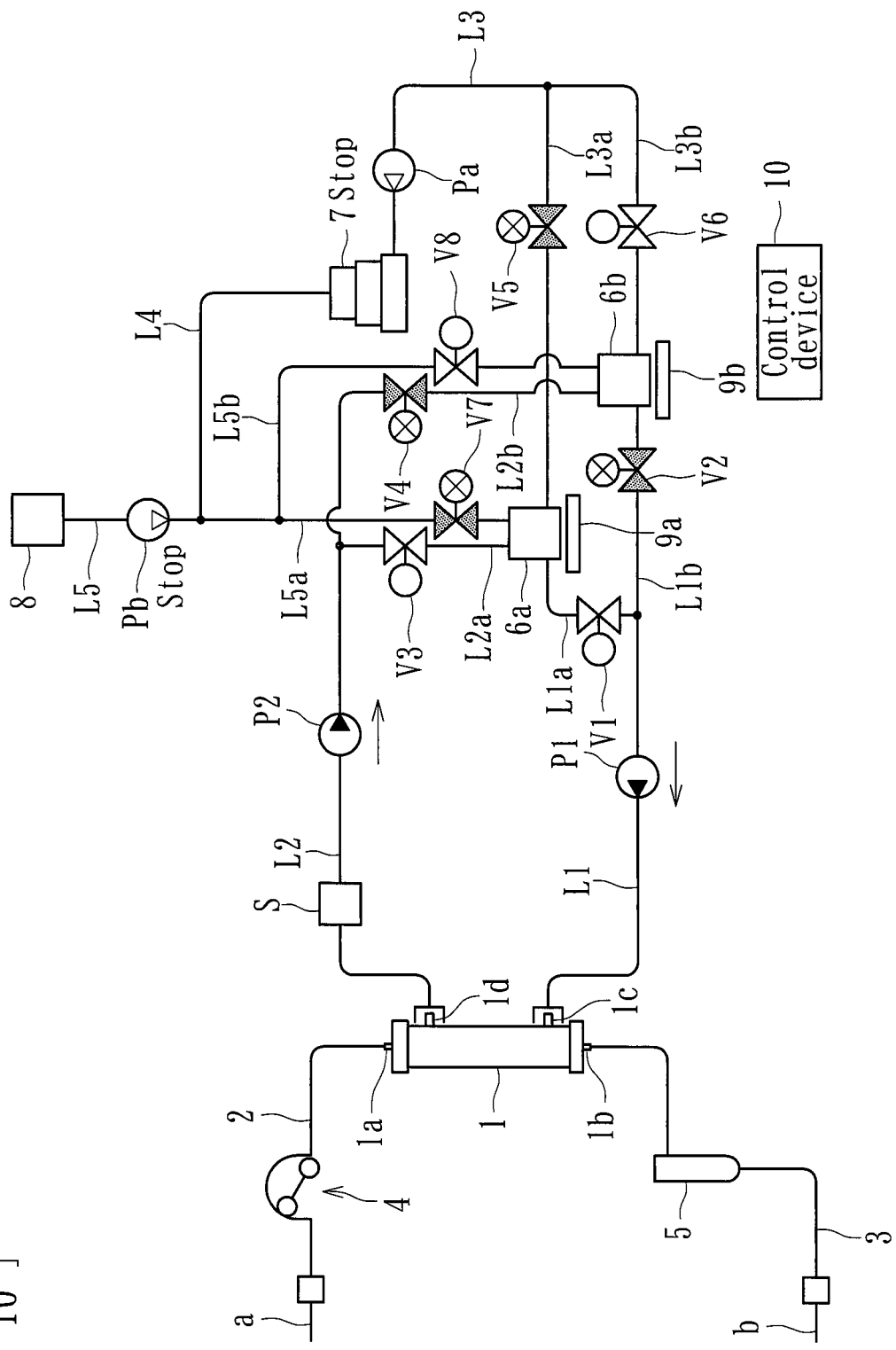
[Fig. 10]

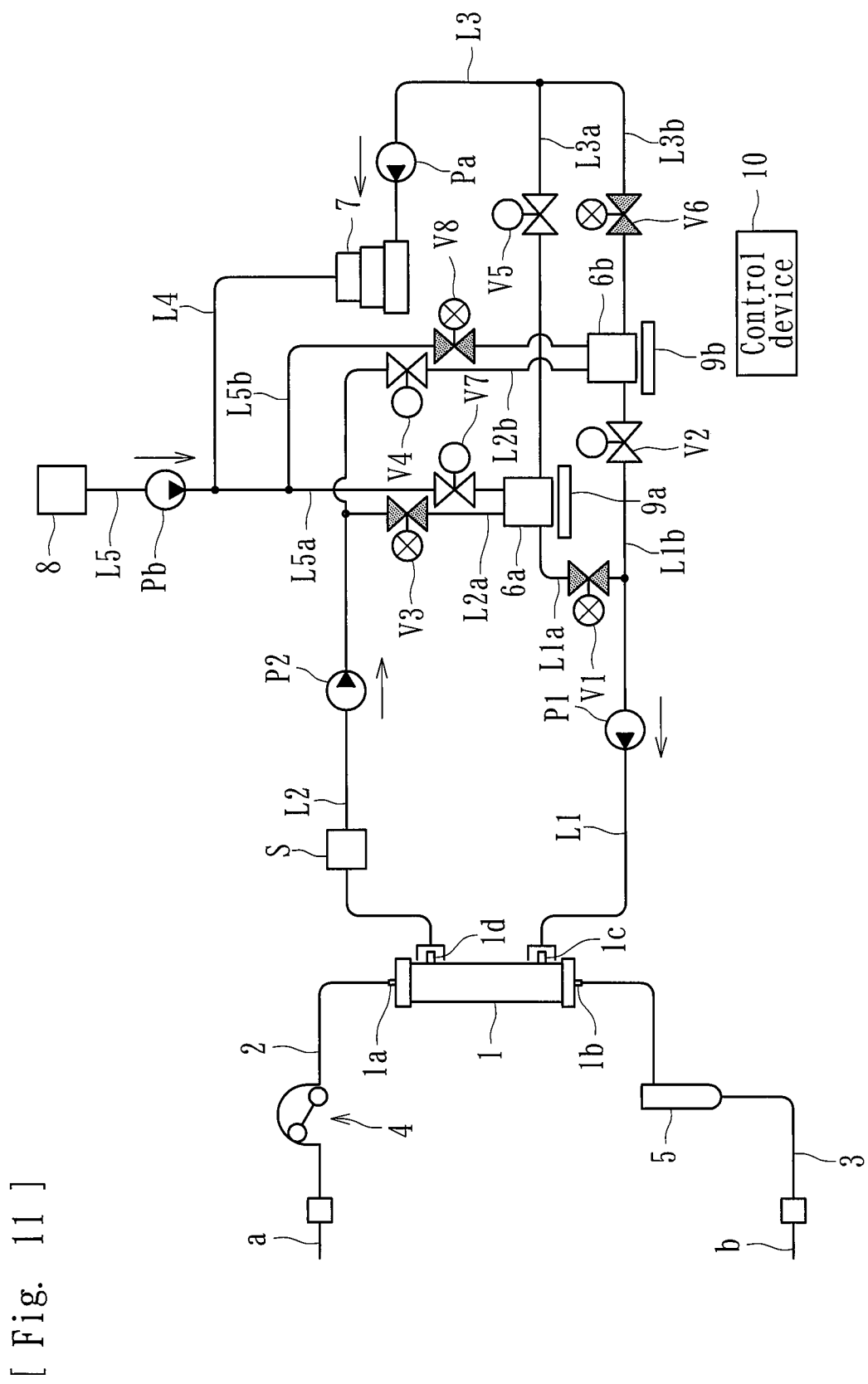
[Fig. 11]

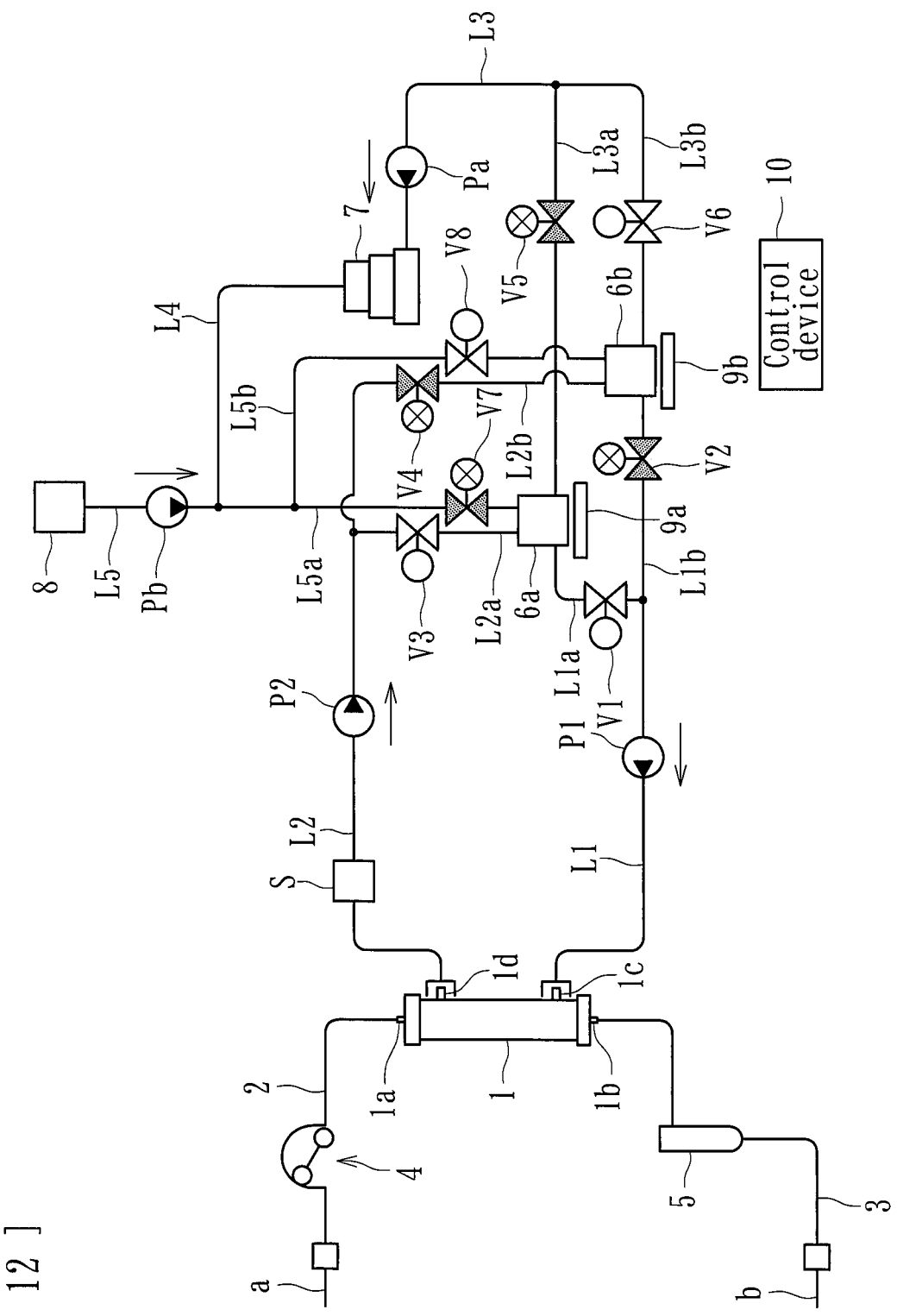
[Fig. 12]

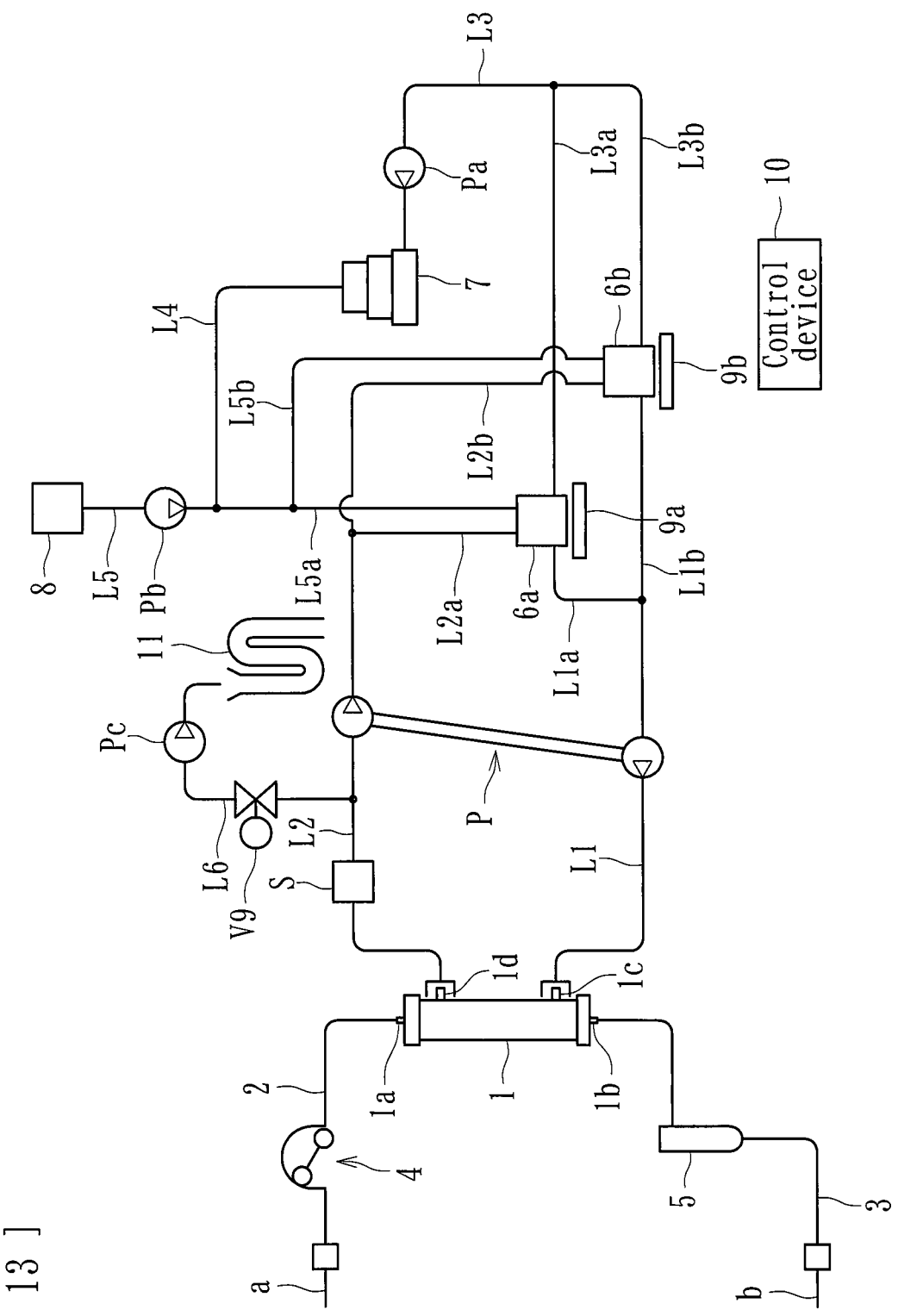
[Fig. 13]

[Fig. 14]
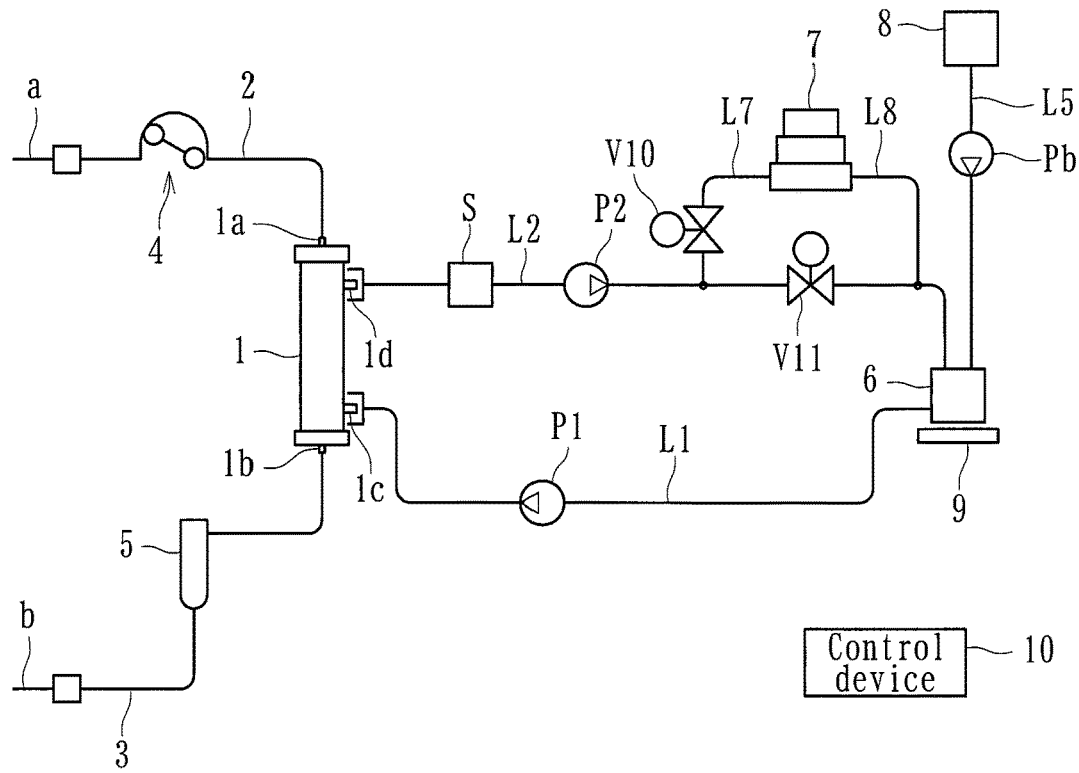
[Fig. 15]
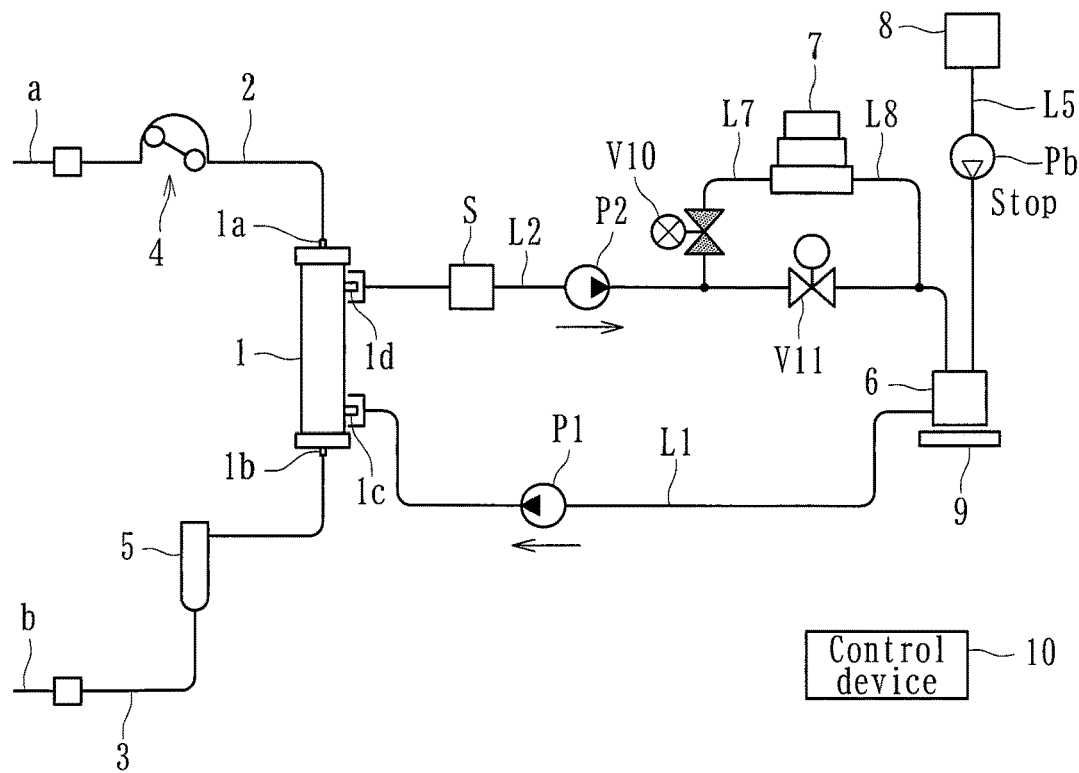

[Fig. 16]
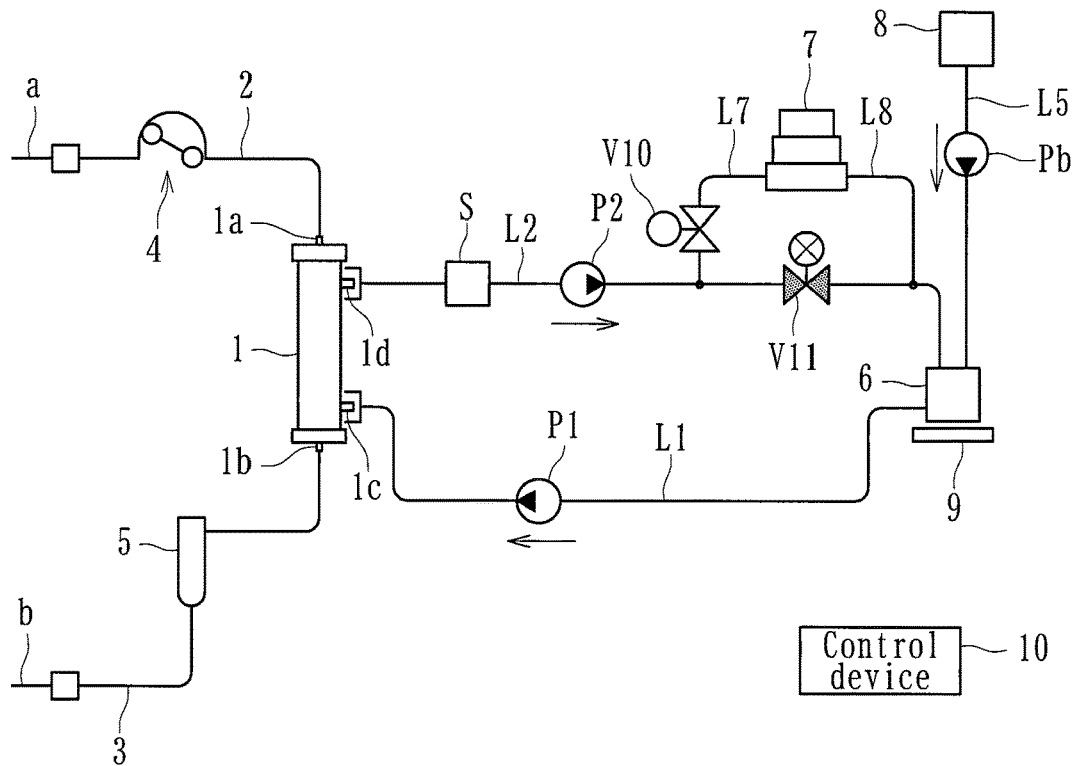
[Fig. 17]
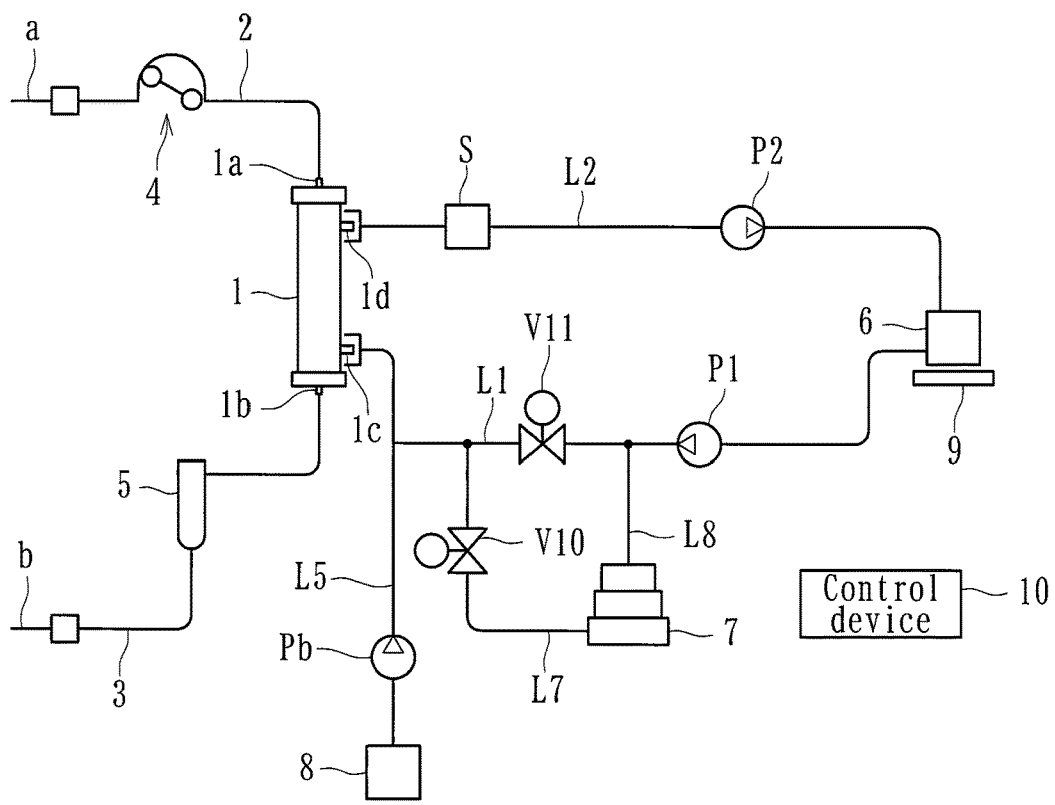

BLOOD PURIFICATION APPARATUS

FIELD

The present invention relates to a blood purification apparatus capable of performing blood purification treatment while causing dialysate to circulate.

BACKGROUND

In general, a blood purification apparatus for giving dialysis treatment includes an arterial blood circuit and a venous blood circuit that form a blood circuit for causing the blood of a patient to extracorporeally circulate, a blood purifier for purifying the blood that extracorporeally circulates through the blood circuit, and an apparatus body provided with various treatment devices such as a blood pump for causing the blood circuit and the blood purifier to perform blood purification treatment. Vascular access catheters or puncture needles (an arterial puncture needle and a venous puncture needle) are attachable to the distal ends of the arterial blood circuit and the venous blood circuit, respectively.

For example, when the blood pump is activated after the arterial puncture needle and the venous puncture needle are stuck into the patient, the blood of the patient extracorporeally circulates through the arterial blood circuit and the venous blood circuit. In this process, the blood is purified by the blood purifier. In the dialysis treatment, a dialysate introduction line for introducing dialysate into the blood purifier and a dialysate drain line for draining waste liquid from the blood purifier are connected to the blood purifier.

For example, as a known blood purification apparatus for general household use, there is a proposal of a circulation-type apparatus including a storage device capable of storing a predetermined amount of dialysate. In the apparatus, the dialysate in the storage device is introduced into a blood purifier, and waste liquid from the blood purifier is returned into the storage device, whereby the dialysate circulates (see PTL 1). In the known circulation-type blood purification apparatus, an adsorbent cartridge (a dialysate purification device) is connected to a dialysate circulation line, and waste matter contained in the waste liquid from the blood purifier is adsorbed and removed, whereby the circulating dialysate can be purified.

PTL 1: JP2014-500733 (a Published Japanese Translation of a PCT Application) the teachings of which are incorporated by references herein for all purposes.

SUMMARY

In the above known blood purification apparatus, however, since the dialysate circulates via the adsorbent cartridge throughout a period from the beginning of the treatment to the end of the treatment, the following problem arises.

The concentration of waste matter contained in the dialysate is high at the beginning of the treatment but usually becomes lower as the treatment time elapses. That is, in latter part of the treatment, the adsorption by the adsorbent cartridge is performed for removing only a small amount of waste matter. Therefore, the efficiency of dialysate purification is low. Furthermore, electrolytes that are necessary for dialysis treatment are also adsorbed. Accordingly, the amount of electrolytes in the dialysate may become short.

The present invention has been conceived in view of the above circumstances and provides a blood purification apparatus with which the efficiency of dialysate purification can be improved and the reduction in the amount of electrolytes contained in the dialysate and necessary for treatment can be suppressed.

DETAILED DESCRIPTION

According to the teachings herein, there is provided a blood purification apparatus including a blood circuit through which blood of a patient is allowed to extracorporeally circulate, a blood purification device that purifies the blood flowing in the blood circuit, a storage device capable of storing a predetermined amount of dialysate that is necessary for blood purification treatment, a dialysate circulation line through which the dialysate is allowed to circulate by introducing the dialysate in the storage device into the blood purification device and draining waste liquid from the blood purification device into the storage device, and a dialysate purification device that purifies the dialysate in the dialysate circulation line. A treatment state in which the dialysate circulating through the dialysate circulation line is allowed to be introduced into the blood purification device without flowing through the dialysate purification device and a purification state in which the dialysate in the dialysate circulation line is allowed to be purified by the dialysate purification device are taken switchably. The purification state is taken if a predetermined condition is satisfied after a start of the treatment state.

According to the teachings herein, in the blood purification apparatus taught herein, the treatment state and the purification state are taken alternately during blood purification treatment.

According to the teachings herein, the blood purification apparatus taught herein further includes a substitution-fluid supply device capable of supplying substitution fluid containing electrolytes that are necessary for blood purification treatment to the dialysate before the dialysate purified by the dialysate purification device reaches the blood purification device.

According to the teachings herein, in the blood purification apparatus taught herein, the predetermined condition is defined as an estimated time taken for a concentration of waste matter in the dialysate circulating through the dialysate circulation line to reach a predetermined concentration after the start of the treatment state.

According to the teachings herein, the blood purification apparatus taught herein further includes a waste-matter-concentration measurement device capable of measuring a concentration of waste matter in the dialysate circulating through the dialysate circulation line. The predetermined condition is defined as reaching of the concentration of waste matter measured by the waste-matter-concentration measurement device to a predetermined concentration after the start of the treatment state.

According to the teachings herein, in the blood purification apparatus taught herein, the storage device includes a first storage device and a second storage device in each of which a predetermined amount of dialysate is stored. The dialysate circulation line includes a first circulation-route system through which the dialysate in the first storage device is allowed to circulate via the blood purification device, and a second circulation-route system through which the dialysate in the second storage device is allowed to circulate via the blood purification device. When one of the first circulation-route system and the second circulation-route system is in the treatment state, an other is in the purification state.

According to the teachings herein, the blood purification apparatus taught herein further includes a detour line to which the dialysate purification device is provided and that allows the dialysate flowing in the dialysate circulation line to detour. The flow into the detour line is prevented in the treatment state, whereas the dialysate is allowed to flow into the detour line and to be purified by the dialysate purification device in the purification state.

According to the teachings herein, the treatment state in which the dialysate circulating through the dialysate circulation line is allowed to be introduced into the blood purification device without flowing through the dialysate purification device and the purification state in which the dialysate in the dialysate circulation line is allowed to be purified by the dialysate purification device are taken switchably. Furthermore, the purification state is taken if the predetermined condition is satisfied after the start of the treatment state. Therefore, the efficiency of dialysate purification can be improved, and the reduction in the amount of electrolytes in the dialysate that are necessary for the treatment can be suppressed.

According to the teachings herein, the treatment state and the purification state are taken alternately during blood purification treatment. Therefore, blood purification treatment can be performed regularly with purified dialysate.

According to the teachings herein, the blood purification apparatus further includes the substitution-fluid supply device capable of supplying the substitution fluid containing electrolytes that are necessary for blood purification treatment to the dialysate before the dialysate purified by the dialysate purification device reaches the blood purification device. Therefore, the occurrence of shortage of electrolytes in the dialysate during blood purification treatment can be prevented.

According to the teachings herein, the predetermined condition is defined as the estimated time taken for the concentration of waste matter in the dialysate circulating through the dialysate circulation line to reach the predetermined concentration after the start of the treatment state. Therefore, the switching from the treatment state to the purification state can be realized simply and easily.

According to the teachings herein, the blood purification apparatus further includes the waste-matter-concentration measurement device capable of measuring the concentration of waste matter in the dialysate circulating through the dialysate circulation line. Furthermore, the predetermined condition is defined as the reaching of the concentration of waste matter measured by the waste-matter-concentration measurement device to the predetermined concentration after the start of the treatment state. Therefore, the switching from the treatment state to the purification state can be realized assuredly and smoothly.

According to the teachings herein, when one of the first circulation-route system and the second circulation-route system is in the treatment state, the other is in the purification state. Therefore, the dialysate can be purified while the blood purification treatment is performed continuously.

According to the teachings herein, the flow into the detour line is prevented in the treatment state, whereas the dialysate is allowed to flow into the detour line and to be purified by the dialysate purification device in the purification state. Therefore, the dialysate can be purified while being made to flow. Moreover, the dialysate can be purified while blood purification treatment is performed continuously.

BRIEF DESCRIPTION OF DRAWINGS

FIG. 1 is a schematic diagram of a blood purification apparatus according to a first embodiment of the present invention.

FIG. 2 is a schematic diagram of the blood purification apparatus in a treatment state.

FIG. 3 is a schematic diagram of the blood purification apparatus in a purification state.

FIG. 4 is a schematic diagram illustrating an embodiment in which a substitution-fluid supply device is connected to a dialysate circulation line.

FIG. 5 is a schematic diagram of a blood purification apparatus according to a second embodiment of the present invention.

FIG. 6 is a schematic diagram of the blood purification apparatus in a treatment state.

FIG. 7 is a schematic diagram of the blood purification apparatus in another treatment state (at the time of ultrafiltration).

FIG. 8 is a schematic diagram of the blood purification apparatus in a purification state.

FIG. 9 is a schematic diagram of a blood purification apparatus according to a third embodiment of the present invention.

FIG. 10 is a schematic diagram of the blood purification apparatus, with a first circulation-route system being in a treatment state and a second circulation-route system being in a stopped state.

FIG. 11 is a schematic diagram of the blood purification apparatus, with the first circulation-route system being in a purification state and the second circulation-route system being in the treatment state.

FIG. 12 is a schematic diagram of the blood purification apparatus, with the first circulation-route system being in the treatment state and the second circulation-route system being in the purification state.

FIG. 13 is a schematic diagram of another embodiment of the blood purification apparatus (including a duplex pump).

FIG. 14 is a schematic diagram of a blood purification apparatus according to a fourth embodiment of the present invention.

FIG. 15 is a schematic diagram of the blood purification apparatus in a treatment state.

FIG. 16 is a schematic diagram of the blood purification apparatus in a purification state.

FIG. 17 is a schematic diagram of an embodiment in which a detour line is connected to a dialysate introduction line.

DESCRIPTION OF EMBODIMENTS

Embodiments of the present invention will now be described specifically with reference to the drawings.

A blood purification apparatus according to a first embodiment is applied to a hemodialysis apparatus and includes, as illustrated in FIG. 1, a blood circuit in which an arterial blood circuit 2 and a venous blood circuit 3 are connected to a dialyzer 1 serving as a blood purification device, a storage device 6, a dialysate circulation line including a dialysate introduction line L1 and a dialysate drain line L2, pumps P1 and P2, a waste-matter-concentration measurement device (S), a dialysate purification device 7, a substitution-fluid supply device 8, and a control device 10.

The dialyzer 1 has non-illustrated blood purification membranes (hollow-fiber hemodialysis membranes in the present embodiment, or flat-film hemodialysis membranes or the like) therein and is provided with a blood introduction port 1*a* from which blood is introduced, a blood delivery port 1*b* from which the blood thus introduced is delivered, a dialysate introduction port 1*c* from which dialysate is introduced, and a dialysate drain port 1d from which the dialysate thus introduced is drained. The dialyzer 1 purifies the blood by bringing the dialysate into contact, through the hollow fiber membranes, with the blood introduced thereinto from the blood introduction port 1a.

The arterial blood circuit 2 is chiefly formed of a flexible tube, with one end thereof connected to the blood introduction port 1a of the dialyzer 1, thereby introducing blood collected from a blood vessel of a patient into the hollow fiber membranes provided in the dialyzer 1. The other end of the arterial blood circuit 2 is provided with a connector for attaching an arterial (blood-removal-side or blood-collection-side) puncture needle (a), and is also provided with a blood pump 4. The blood pump 4 is a peristaltic pump (configured to squeeze the flexible tube when rotated in the normal direction, thereby causing the blood to flow from the side of the arterial puncture needle a toward the blood introduction port 1a of the dialyzer 1).

The venous blood circuit 3 is chiefly formed of a flexible tube, as with the arterial blood circuit 2, with one end thereof connected to the blood delivery port 1b of the dialyzer 1, thereby delivering the blood having flowed through the hollow fiber membranes. The other end of the venous blood circuit 3 is provided with a connector for attaching a venous (blood-returning-side) puncture needle b, and is also provided with a venous air-trap chamber 5 for bubble removal at a halfway position thereof. That is, the blood of the patient collected from the arterial puncture needle (a) flows through the arterial blood circuit 2, reaches the dialyzer 1, is purified therein, flows through the venous blood circuit 3, and returns into the body of the patient through the venous puncture needle (b). Thus, the blood extracorporeally circulates. In this specification, the side of the puncture needle provided for blood removal (collection) is referred to as the "arterial" side, and the side of the puncture needle provided for returning the blood is referred to as the "venous" side. The "arterial" side and the "venous" side are not defined on the basis of which of the artery and the vein is to be the object of puncture.

An end of the dialysate introduction line L1 and an end of the dialysate drain line L2 are connected to the dialysate introduction port 1c and the dialysate drain port 1d, respectively, of the dialyzer 1. The dialysate introduced into the dialyzer 1 through the dialysate introduction line L1 flows outside the hollow fiber membranes and is allowed to be drained through the dialysate drain line L2. Thus, the inside of each of the hollow fiber membranes (purification membranes) provided in the dialyzer 1 forms a blood flow route in which blood is allowed to flow, whereas the outside of each of the hollow fiber membranes forms a dialysate flow route in which dialysate is allowed to flow.

The dialysate introduction line L1 and the dialysate drain line L2 are also connected to the storage device 6 that is capable of storing a predetermined amount of dialysate necessary for blood purification treatment. The dialysate introduction line L1 is provided with the pump P1, and the dialysate drain line L2 is provided with the pump P2. The storage device 6 is formed of a storage tank, a storage bag, or the like that is capable of storing a predetermined amount of dialysate. When the pumps P1 and P2 are activated, the dialysate in the storage device 6 is introduced into the dialyzer 1 through the dialysate introduction line L1 and waste liquid (dialysate containing waste matter) discharged from the dialyzer 1 is drained into the storage device 6.

Thus, the dialysate introduction line L1 and the dialysate drain line L2 form a dialysate circulation line through which the dialysate is allowed to circulate such that the dialysate in the storage device 6 is introduced into the dialyzer 1 and the waste liquid from the dialyzer 1 is drained into the storage device 6. With the activation of the blood pump 4, the blood of the patient extracorporeally circulates, and the dialysate circulates through the dialysate circulation line, whereby blood purification treatment (dialysis treatment) is performed. In the present embodiment, if the flow rate of the pump P2 is set to a greater value than the flow rate of the pump P1, ultrafiltration (removal of water from the blood flowing in the blood flow routes by ultrafiltering the blood through the hollow fiber membranes into the dialysate flow routes) can be performed.

The dialysate drain line L2 is provided with the waste-matter-concentration measurement device (S) that is capable of measuring the concentration of waste matter in the dialysate circulating through the dialysate circulation line. The waste-matter-concentration measurement device (S) is formed of, for example, a waste-liquid-concentration sensor attached to the dialysate drain line L2 and is capable of detecting the concentration of the waste liquid (the concentration of waste matter) drained from the dialyzer 1 during blood purification and thus monitoring the efficiency of blood purification. The waste-matter-concentration measurement device (S) according to the present embodiment is capable of applying light to the circulating dialysate and receiving the light transmitted through the dialysate. The waste-matter-concentration measurement device S is capable of measuring the concentration of waste matter on the basis of the voltage generated in accordance with the intensity of the light received. Alternatively, a waste-matter-concentration measurement device of another type may be employed, as long as the device is capable of measuring the concentration of waste matter.

The dialysate purification device 7 is a so-called column that is capable of adsorbing waste matter contained in the dialysate. The dialysate purification device 7 is configured to purify the dialysate circulating through the dialysate circulation line. The dialysate purification device 7 includes, for example, a container including a plurality of layers stacked thereinside in the vertical direction. The layers include a layer containing activated carbon for adsorbing waste matter (organic metabolite) contained in the dialysate; a purification layer that adsorbs noble metals, oxides, and particles; a decomposition layer that decomposes urea; a layer containing zirconium orthophosphate that adsorbs $Mg^{2+}$, $K^+$, $NH_4^+$, and $Ca^{2+}$ from the dialysate and releases $H^+$ and $Na^+$; a layer containing zirconium oxide that adsorbs phosphorus and fluorine from the dialysate and releases acetate; and so forth.

The dialysate purification device 7 has an introduction port from which dialysate is introduced into the layers provided thereinside, and a delivery port from which the dialysate having flowed through the layers thereinside is delivered. A flow route L3 that guides the dialysate from the storage device 6 into the dialysate purification device 7 is provided between the introduction port and the storage device 6. A flow route L4 that guides the dialysate purified by the dialysate purification device 7 into the storage device 6 is provided between the delivery port and the storage device 6. The flow route L3 is provided with a pump Pa. When the pump Pa is activated, the dialysate in the storage device 6 is introduced into the dialysate purification device 7 and the dialysate purified with the adsorption of waste matter by the dialysate purification device 7 is returned into the storage device 6. Thus, the dialysate can circulate.

The substitution-fluid supply device 8 is connected to the flow route L4 with a substitution-fluid supply line L5 interposed therebetween. The substitution-fluid supply line L5 is provided with a pump Pb. The substitution-fluid supply device 8 stores a predetermined amount of substitution fluid containing electrolytes ($Mg^{2+}$, $K^+$, $Ca^{2+}$, and so forth) necessary for blood purification treatment (dialysis treatment). When the pump Pb is activated, the substitution fluid can be supplied to the storage device 6 through the flow route L4. The substitution-fluid supply device 8 (the same as those employed in the other embodiments) only needs to be capable of supplying substitution fluid to the dialysate before the dialysate purified by the dialysate purification device 7 reaches the dialyzer 1 (the blood purification device). In the present embodiment, a weighing machine 9 capable of weighing the dialysate stored in the storage device 6 is provided so that the amount of substitution fluid supplied from the substitution-fluid supply device 8 can be measured.

The control device 10 is, for example, a microcomputer or the like provided in the apparatus body. The control device 10 is capable of selectively activating or stopping actuators such as the blood pump 4, the pumps P1 and P2, and the pumps Pa and Pb and is electrically connected to the weighing machine 9 and sensors such as the waste-product-concentration measurement device (S). Blood purification treatment is performed under the control of the control device 10.

In the present embodiment, a treatment state (see FIG. 2) in which the dialysate circulating through the dialysate circulation line (the dialysate introduction line L1 and the dialysate drain line L2) is allowed to be introduced into the dialyzer 1 without flowing through the dialysate purification device 7 and a purification state (see FIG. 3) in which the dialysate circulated through the dialysate circulation line (the dialysate introduction line L1 and the dialysate drain line L2) is allowed to be purified by the dialysate purification device 7 are taken switchably. After the start of the treatment state, if a predetermined condition is satisfied, the purification state is taken.

In the treatment state, as illustrated in FIG. 2, the pumps P1 and P2 are activated, but the pumps Pa and Pb are stopped, whereby the dialysate in the storage device 6 circulates through the dialysate introduction line L1 and the dialysate drain line L2. Thus, the dialyzer 1 performs blood purification treatment. In the purification state, as illustrated in FIG. 3, the pumps P1 and P2 are stopped, but the pump Pa is activated, whereby the dialysate in the storage device 6 circulates through the flow routes L3 and L4. Thus, the dialysate purification device 7 purifies the dialysate.

In the purification state, the pump Pb is also activated. When the weighing machine 9 detects the supply of a predetermined amount of substitution fluid to the storage device 6, the pump Pb is stopped. Thus, the electrolytes adsorbed by the dialysate purification device 7 in the purification state can be resupplied to the dialysate to be made to circulate. Hence, preferable blood purification treatment can be performed continuously.

In the present embodiment, the predetermined condition for taking the purification state after the start of the treatment state is the reaching of the concentration of waste matter measured by the waste-matter-concentration measurement device (S) to a predetermined concentration after the start of the treatment state. That is, after the start of the treatment state, when the concentration of waste matter measured by the waste-matter-concentration measurement device (S) reaches a predetermined concentration (a predetermined concentration at which the dialysate needs to be purified), the purification state is taken. Thus, the dialysate in the storage device 6 is purified by the dialysate purification device 7.

In the purification state, when the concentration of waste matter measured by the waste-matter-concentration measurement device (S) reaches a predetermined concentration (a predetermined concentration that is reached when the dialysate has been purified), the treatment state is taken again, whereby the dialysate in the storage device 6 circulates through the flow routes L3 and L4 so as to be purified by the dialysate purification device 7. In the present embodiment, the treatment state and the purification state are taken alternately during blood purification treatment.

The predetermined condition for taking the purification state after the start of the treatment state is not limited to the above-described reaching of the concentration of waste matter measured by the waste-matter-concentration measurement device (S) to the predetermined concentration, and may be an estimated time taken for the concentration of waste matter in the dialysate circulating through the dialysate circulation line (the dialysate introduction line L1 and the dialysate drain line L2) to reach the predetermined concentration (the predetermined concentration at which the dialysate needs to be purified) after the start of the treatment state. In such a case, it is preferable that, in the purification state, the treatment state be taken again at the elapse of the estimated time taken for the concentration of waste matter in the dialysate to reach the predetermined concentration (the predetermined concentration that is reached when the dialysate has been purified).

According to the first embodiment, the treatment state in which the dialysate circulating through the dialysate circulation line (the dialysate introduction line L1 and the dialysate drain line L2) is allowed to be introduced into the dialyzer 1 without flowing through the dialysate purification device 7 and the purification state in which the dialysate circulated through the dialysate circulation line (the dialysate introduction line L1 and the dialysate drain line L2) is allowed to be purified by the dialysate purification device 7 are taken switchably. Furthermore, if the predetermined condition is satisfied after the start of the treatment state, the purification state is taken. Therefore, the efficiency of dialysate purification can be improved, and the reduction in the amount of electrolytes in the dialysate that are necessary for the treatment can be suppressed. Furthermore, according to the present embodiment, the amount of substitution fluid used for resupplying electrolytes that are adsorbed by the dialysate purification device 7 can be reduced.

Furthermore, the treatment state and the purification state are taken alternately during blood purification treatment. Therefore, blood purification treatment can be performed regularly with purified dialysate. Furthermore, the substitution-fluid supply device 8 capable of supplying to the storage device 6 the substitution fluid containing electrolytes that are necessary for blood purification treatment is provided. Therefore, the occurrence of shortage of electrolytes in the dialysate during blood purification treatment can be prevented.

Furthermore, the waste-matter-concentration measurement device (S) capable of measuring the concentration of waste matter contained in the dialysate circulating through the dialysate circulation line (the dialysate introduction line L1 and the dialysate drain line L2) is provided, and the predetermined condition for taking the purification state after the start of the treatment state is defined as the reaching of the concentration of waste matter measured by the waste-matter-concentration measurement device (S) to the predetermined concentration after the start of the treatment state. Therefore, the switching from the treatment state to the purification state can be realized assuredly and smoothly.

If the predetermined condition for taking the purification state after the start of the treatment state is defined as the estimated time taken for the concentration of waste matter in the dialysate circulating through the dialysate circulation line (the dialysate introduction line L1 and the dialysate drain line L2) to reach the predetermined concentration after the start of the treatment state, the switching from the treatment state to the purification state can be realized simply and easily. If the predetermined condition is defined as the estimated time, the switching from the treatment state to the purification state can be realized even in a blood purification apparatus that does not include the waste-matter-concentration measurement device (S).

In the present embodiment, the substitution-fluid supply line L5 is connected to the flow route L4, whereby the substitution fluid in the substitution-fluid supply device 8 can be supplied to the storage device 6 through the flow route L4. Alternatively, as illustrated in FIG. 4 for example, the substitution-fluid supply line L5 may be connected to the dialysate drain line L2 so that the substitution fluid in the substitution-fluid supply device 8 can be supplied to the storage device 6 through the dialysate drain line L2.

Now, a blood purification apparatus according to a second embodiment of the present invention will be described.

The blood purification apparatus according to the present embodiment is applied to a hemodialysis apparatus, as with the case of the above embodiment, and includes, as illustrated in FIG. 5, a blood circuit in which an arterial blood circuit 2 and a venous blood circuit 3 are connected to a dialyzer 1 serving as a blood purification device, a storage device 6, a dialysate circulation line including a dialysate introduction line L1 and a dialysate drain line L2, a duplex pump P, an ultrafiltration pump Pc, a waste-matter-concentration measurement device S, a dialysate purification device 7, a substitution-fluid supply device 8, and a control device 10. Elements that are the same as those employed in the above embodiment are denoted by corresponding ones of the reference numerals, and detailed description of such elements is omitted.

The duplex pump P is provided over the dialysate introduction line L1 and the dialysate drain line L2. The duplex pump P introduces the dialysate in the storage device 6 into the dialyzer 1 and drains the dialysate having undergone dialysis from the dialyzer 1 into the storage device 6. The dialysate drain line L2 is provided with a flow route L6 through which dialysate is allowed to flow. The flow route L6 is connected to the dialysate drain line L2 on the upstream side (nearer to the dialyzer 1) with respect to the duplex pump P. The flow route L6 is provided with the ultrafiltration pump Pc.

The flow route L6 is provided at a distal end thereof with a dialysate drain device 11 for draining the dialysate to the outside of the apparatus. When the ultrafiltration pump Pc is activated, the dialysate in the dialysate drain line L2 flows into the flow route L6 and reaches the dialysate drain device 11, from which the dialysate is drained to the outside of the apparatus. With the activation of the ultrafiltration pump Pc, the flow rate of the dialysate drained from the dialyzer 1 becomes greater than the flow rate of the dialysate introduced into the dialyzer 1, whereby ultrafiltration can be performed.

In the present embodiment, a treatment state (see FIGS. 6 and 7) in which the dialysate circulating through the dialysate circulation line (the dialysate introduction line L1 and the dialysate drain line L2) is allowed to be introduced into the dialyzer 1 without flowing through the dialysate purification device 7 and a purification state (see FIG. 8) in which the dialysate circulated through the dialysate circulation line (the dialysate introduction line L1 and the dialysate drain line L2) is allowed to be purified by the dialysate purification device 7 are taken switchably. After the start of the treatment state, if a predetermined condition is satisfied, the purification state is taken.

In the treatment state, as illustrated in FIG. 6, the duplex pump P is activated, but the pumps Pa and Pb and the ultrafiltration pump Pc are stopped, whereby the dialysate in the storage device 6 circulates through the dialysate introduction line L1 and the dialysate drain line L2. Thus, the dialyzer 1 performs blood purification treatment. In the treatment state, if the ultrafiltration pump Pc is activated as illustrated in FIG. 7, ultrafiltration can be performed.

In the purification state, as illustrated in FIG. 8, the duplex pump P and the ultrafiltration pump Pc are stopped, but the pump Pa is activated, whereby the dialysate in the storage device 6 circulates through the flow routes L3 and L4. Thus, the dialysate purification device 7 purifies the dialysate. In the purification state, the pump Pb is also activated. When the weighing machine 9 detects the supply of a predetermined amount of substitution fluid to the storage device 6, the pump Pb is stopped. Thus, the electrolytes adsorbed by the dialysate purification device 7 in the purification state can be resupplied to the dialysate to be made to circulate. Hence, preferable blood purification treatment can be performed continuously.

As with the case of the above embodiment, the predetermined condition for taking the purification state after the start of the treatment state is the reaching of the concentration of waste matter measured by the waste-matter-concentration measurement device (S) to the predetermined concentration after the start of the treatment state. That is, after the start of the treatment state, when the concentration of waste matter measured by the waste-matter-concentration measurement device S reaches a predetermined concentration (a predetermined concentration at which the dialysate needs to be purified), the purification state is taken. Thus, the dialysate in the storage device 6 is purified by the dialysate purification device 7.

In the purification state, when the concentration of waste matter measured by the waste-matter-concentration measurement device (S) reaches a predetermined concentration (a predetermined concentration that is reached when the dialysate has been purified), the treatment state is taken again, whereby the dialysate in the storage device 6 circulates through the flow routes L3 and L4 so as to be purified by the dialysate purification device 7. In the present embodiment, the treatment state and the purification state are taken alternately during blood purification treatment.

The predetermined condition for taking the purification state after the start of the treatment state is not limited to the above-described reaching of the concentration of waste matter measured by the waste-matter-concentration measurement device (S) to the predetermined concentration, and may be an estimated time taken for the concentration of waste matter in the dialysate circulating through the dialysate circulation line (the dialysate introduction line L1 and the dialysate drain line L2) to reach the predetermined concentration (the predetermined concentration at which the dialysate needs to be purified) after the start of the treatment state. In such a case, it is preferable that, in the purification state, the treatment state be taken again at the elapse of the estimated time taken for the concentration of waste matter in the dialysate to reach the predetermined concentration (the predetermined concentration that is reached when the dialysate has been purified).

According to the second embodiment, the treatment state in which the dialysate circulating through the dialysate circulation line (the dialysate introduction line L1 and the dialysate drain line L2) is allowed to be introduced into the dialyzer 1 without flowing through the dialysate purification device 7 and the purification state in which the dialysate circulated through the dialysate circulation line (the dialysate introduction line L1 and the dialysate drain line L2) is allowed to be purified by the dialysate purification device 7 are taken switchably. Furthermore, if the predetermined condition is satisfied after the start of the treatment state, the purification state is taken. Therefore, the efficiency of dialysate purification can be improved, and the reduction in the amount of electrolytes in the dialysate that are necessary for the treatment can be suppressed. Furthermore, according to the present embodiment, the amount of substitution fluid used for resupplying electrolytes that are adsorbed by the dialysate purification device 7 can be reduced.

Furthermore, the treatment state and the purification state are taken alternately during blood purification treatment. Therefore, blood purification treatment can be performed regularly with purified dialysate. Furthermore, the substitution-fluid supply device 8 capable of supplying to the storage device 6 the substitution fluid containing electrolytes that are necessary for blood purification treatment is provided. Therefore, the occurrence of shortage of electrolytes in the dialysate during blood purification treatment can be prevented.

Furthermore, the waste-matter-concentration measurement device S capable of measuring the concentration of waste matter contained in the dialysate circulating through the dialysate circulation line (the dialysate introduction line L1 and the dialysate drain line L2) is provided, and the predetermined condition for taking the purification state after the start of the treatment state is defined as the reaching of the concentration of waste matter measured by the waste-matter-concentration measurement device (S) to the predetermined concentration after the start of the treatment state. Therefore, the switching from the treatment state to the purification state can be realized assuredly and smoothly.

If the predetermined condition for taking the purification state after the start of the treatment state is defined as the estimated time taken for the concentration of waste matter in the dialysate circulating through the dialysate circulation line (the dialysate introduction line L1 and the dialysate drain line L2) to reach the predetermined concentration after the start of the treatment state, the switching from the treatment state to the purification state can be realized simply and easily. If the predetermined condition is defined as the estimated time, the switching from the treatment state to the purification state can be realized even in a blood purification apparatus that does not include the waste-matter-concentration measurement device S.

Now, a blood purification apparatus according to a third embodiment of the present invention will be described.

The blood purification apparatus according to the present embodiment is applied to a hemodialysis apparatus, as with the cases of the above embodiments, and includes, as illustrated in FIG. 9, a blood circuit in which an arterial blood circuit 2 and a venous blood circuit 3 are connected to a dialyzer 1 serving as a blood purification device, a first storage device 6a and a second storage device 6b, a dialysate circulation line (a first circulation-route system and a second circulation-route system) including a dialysate introduction line L1 and a dialysate drain line L2, pumps P1 and P2, a waste-matter-concentration measurement device (S), a dialysate purification device 7, a substitution-fluid supply device 8, and a control device 10. Elements that are the same as those employed in either of the above embodiments are denoted by corresponding ones of the reference numerals, and detailed description of such elements is omitted.

The first storage device 6a and the second storage device 6b are each a tank or the like in which a predetermined amount of dialysate is stored. The blood purification apparatus includes a flow route L1a connected to the first storage device 6a and to the dialysate introduction line L1 and through which the dialysate is allowed to flow, a flow route L2a connected to the first storage device 6a and to the dialysate drain line L2 and through which the dialysate is allowed to flow, a flow route L1b connected to the second storage device 6b and to the dialysate introduction line L1 and through which the dialysate is allowed to flow, and a flow route L2b connected to the second storage device 6b and to the dialysate drain line L2 and through which the dialysate is allowed to flow.

The flow route L1a and the flow route L1b are provided with electromagnetic valves V1 and V2, respectively. The flow route L2a and the flow route L2b are provided with electromagnetic valves V3 and V4, respectively. The control device 10 is capable of controlling the opening and the closing of any of the electromagnetic valves. When the electromagnetic valves V1 and V3 are opened with the electromagnetic valves V2 and V4 being closed, the flow route L1a, the dialysate introduction line L1, the dialysate drain line L2, and the flow route L2a form a first circulation-route system through which the dialysate in the first storage device 6a is allowed to circulate via the dialyzer 1. When the electromagnetic valves V1 and V3 are closed with the electromagnetic valves V2 and V4 being open, the flow route L1b, the dialysate introduction line L1, the dialysate drain line L2, and the flow route L2b form a second circulation-route system through which the dialysate in the second storage device 6b is allowed to circulate via the dialyzer 1. That is, the dialysate circulation line having the first storage device 6a forms the first circulation-route system, and the dialysate circulation line having the second storage device 6b forms the second circulation-route system.

The first storage device 6a is connected to the flow route L3 with a flow route L3a, through which the dialysate is allowed to flow, interposed therebetween and is also connected to a flow route L5 with a flow route L5a, through which the dialysate is allowed to flow, interposed therebetween. The second storage device 6b is connected to the flow route L3 with a flow route L3b, through which the dialysate is allowed to flow, interposed therebetween and is also connected to the flow route L5 with a flow route L5b, through which the dialysate is allowed to flow, interposed therebetween. The flow route L4 extending from the dialysate purification device 7 is connected to the flow route L5. The flow route L3a and the flow route L3b are provided with electromagnetic valves V5 and V6, respectively. The flow route L5a and the flow route L5b are provided with electromagnetic valves V7 and V8, respectively. The control device 10 is capable of controlling the opening and the closing of any of the electromagnetic valves.

In the present embodiment, when one of the first circulation-route system and the second circulation-route system is in the treatment state, the other is in the purification state. Specifically, as illustrated in FIGS. 10 and 12, when the electromagnetic valves V1, V3, V6, and V8 are opened with the electromagnetic valves V2, V4, V5, and V7 being closed, the first circulation-route system (the dialysate circulation line having the first storage device 6a) takes the treatment state, whereas the second circulation-route system (the dialysate circulation line having the second storage device 6b) takes the purification state (note that FIG. 10 illustrates a stopped state where the pumps Pa and Pb are stopped). On the other hand, as illustrated in FIG. 11, when the electromagnetic valves V2, V4, V5, and V7 are opened with the electromagnetic valves V1, V3, V6, and V8 being closed, the first circulation-route system takes the purification state, whereas the second circulation-route system takes the treatment state.

In the first circulation-route system and the second circulation-route system, as with the cases of the above embodiments, the purification state is taken if a predetermined condition is satisfied after the start of the treatment state. The predetermined condition is the same as those described in the above embodiments. Specifically, as illustrated in FIG. 10, when the pumps P1 and P2 are activated with the pumps Pa and Pb being stopped and the electromagnetic valves V1, V3, V6, and V8 are opened with the electromagnetic valves V2, V4, V5, and V7 being closed, the first circulation-route system takes the treatment state (in this case, the second circulation-route system is in the stopped state because purification is not necessary yet).

If the predetermined condition is satisfied after the first circulation-route system starts to take the treatment state, when the pumps P1 and P2 and the pumps Pa and Pb are activated and the electromagnetic valves V2, V4, V5, and V7 are opened with the electromagnetic valves V1, V3, V6, and V8 being closed as illustrated in FIG. 11, the first circulation-route system takes the purification state, whereas the second circulation-route system takes the treatment state. If the predetermined condition is satisfied after the second circulation-route system starts to take the treatment state, when the pumps P1 and P2 and the pumps Pa and Pb are activated and the electromagnetic valves V1, V3, V6, and V8 are opened with the electromagnetic valves V2, V4, V5, and V7 being closed as illustrated in FIG. 12, the first circulation-route system takes the treatment state, whereas the second circulation-route system takes the purification state.

As described above, when one of the first circulation-route system and the second circulation-route system is in the treatment state, the other is in the purification state (in the present embodiment, immediately after the start of the treatment and when the first circulation-route system is in the treatment state, the second circulation-route system is still stopped). That is, the treatment state and the purification state are taken alternately as illustrated in FIGS. 11 and 12 during blood purification treatment. Thus, the dialysate can be purified while the blood purification treatment is performed continuously.

According to the third embodiment, for each of the first circulation-route system and the second circulation-route system, the treatment state in which the dialysate circulating through the dialysate circulation line (the dialysate introduction line L1 and the dialysate drain line L2) is allowed to be introduced into the dialyzer 1 without flowing through the dialysate purification device 7 and the purification state in which the dialysate circulated through the dialysate circulation line (the dialysate introduction line L1 and the dialysate drain line L2) is allowed to be purified by the dialysate purification device 7 are taken switchably. Furthermore, if the predetermined condition is satisfied after the start of the treatment state, the purification state is taken. Therefore, the efficiency of dialysate purification can be improved, and the reduction in the amount of electrolytes in the dialysate that are necessary for the treatment can be suppressed. Furthermore, according to the present embodiment, the amount of substitution fluid used for resupplying electrolytes that are adsorbed by the dialysate purification device 7 can be reduced.

Furthermore, the treatment state and the purification state are taken alternately during blood purification treatment. Therefore, blood purification treatment can be performed regularly with purified dialysate. Furthermore, the substitution-fluid supply device 8 capable of supplying to the storage device 6 the substitution fluid containing electrolytes that are necessary for blood purification treatment is provided. Therefore, the occurrence of shortage of electrolytes in the dialysate during blood purification treatment can be prevented.

In the above third embodiment, as illustrated in FIG. 13, the pumps P1 and P2 may be replaced with the duplex pump P provided over the dialysate introduction line L1 and the dialysate drain line L2, as with the case of the second embodiment, and a flow route L6 provided with the ultrafiltration pump Pc may be provided in such a manner as to extend from the dialysate drain line L2. In such a case, with the activation of the ultrafiltration pump Pc, the flow rate of the dialysate drained from the dialyzer 1 becomes greater than the flow rate of the dialysate introduced into the dialyzer 1, whereby ultrafiltration can be performed. As illustrated in FIG. 13, it is preferable to provide an electromagnetic valve V9 to the flow route L6 and to open the electromagnetic valve V9 at the time of ultrafiltration.

Now, a blood purification apparatus according to a fourth embodiment of the present invention will be described.

The blood purification apparatus according to the present embodiment is applied to a hemodialysis apparatus, as with the cases of the above embodiments, and includes, as illustrated in FIG. 14, a blood circuit in which an arterial blood circuit 2 and a venous blood circuit 3 are connected to a dialyzer 1 serving as a blood purification device, a storage device 6, a dialysate circulation line including a dialysate introduction line L1 and a dialysate drain line L2, detour lines L7 and L8, pumps P1 and P2, a waste-matter-concentration measurement device (S), a dialysate purification device 7, a substitution-fluid supply device 8, and a control device 10. Elements that are the same as those employed in any of the above embodiments are denoted by corresponding ones of the reference numerals, and detailed description of such elements is omitted.

The detour lines L7 and L8 form a flow route that allows the dialysate flowing in the dialysate circulation line (in the present embodiment, the dialysate drain line L2, which is one of the dialysate introduction line L1 and the dialysate drain line L2 that form the dialysate circulation line) to detour therefrom and that is provided with the dialysate purification device 7. The detour line L7 is provided with an electromagnetic valve V10. The dialysate introduction line L1 is provided with an electromagnetic valve V11 at a position thereof between the connection to the detour line L7 and the connection to the detour line L8.

In the treatment state, as illustrated in FIG. 15, the electromagnetic valve V10 is closed but the electromagnetic valve V11 is opened, whereby the flow into the detour lines L7 and L8 is prevented. In the purification state, as illustrated in FIG. 16, the electromagnetic valve V10 is opened but the electromagnetic valve V11 is closed, whereby the dialysate is allowed to flow into the detour lines L7 and L8 and to be purified by the dialysate purification device 7.

In the present embodiment, as with the cases of the above embodiments, if the predetermined condition is satisfied after the start of the treatment state (see FIG. 15), the purification state (see FIG. 16) is taken. The predetermined condition is the same as those described in the above embodiments. Specifically, in the treatment state, as illustrated in FIG. 15, the pumps P1 and P2 are activated but the pump Pb is stopped, and the electromagnetic valve V10 is closed but the electromagnetic valve V11 is opened. Thus, the dialysate in the storage device 6 flows into the dialysate introduction line L1 and reaches the dialyzer 1, where the blood is purified. Then, the dialysate flows into the dialysate drain line L2, without flowing into the detour lines L7 and L8, and is drained into the storage device 6. Thus, the dialysate in the storage device 6 is allowed to circulate through the dialysate introduction line L1 and the dialysate drain line L2.

In the purification state, as illustrated in FIG. 16, the pumps P1 and P2 are activated and the pump Pb is also activated, and the electromagnetic valve V10 is opened but the electromagnetic valve V11 is closed. Thus, the dialysate in the storage device 6 flows into the dialysate introduction line L1 and reaches the dialyzer 1. After the blood is purified with the dialysate thus flowed into the dialyzer 1, the resulting waste liquid flows into the detour lines L7 and L8 and is purified by the dialysate purification device 7. Then, the waste liquid is drained into the storage device 6 through the dialysate drain line L2. Thus, the dialysate in the storage device 6 can be purified by the dialysate purification device 7 in the process of circulating through the dialysate introduction line L1 and the dialysate drain line L2.

As described above, the flow into the detour lines L7 and L8 is prevented in the treatment state, whereas the dialysate is allowed to flow into the detour lines L7 and L8 and to be purified by the dialysate purification device 7 in the purification state. Hence, the dialysate can be purified while being made to flow. Moreover, the dialysate can be purified while blood purification treatment is performed continuously. In the present embodiment, the detour lines L7 and L8 provided with the dialysate purification device 7 are connected to the dialysate drain line L2. Alternatively, as illustrated in FIG. 17, the detour lines L7 and L8 may be connected to the dialysate introduction line L1. Furthermore, the pumps P1 and P2 may be replaced with the duplex pump employed in the second embodiment.

According to the fourth embodiment, the treatment state in which the dialysate circulating through the dialysate circulation line (the dialysate introduction line L1 and the dialysate drain line L2) is allowed to be introduced into the dialyzer 1 without flowing through the dialysate purification device 7 and the purification state in which the dialysate in the dialysate circulation line (the dialysate introduction line L1 and the dialysate drain line L2) is allowed to be purified by the dialysate purification device 7 are taken switchably. Furthermore, if the predetermined condition is satisfied after the start of the treatment state, the purification state is taken. Therefore, the efficiency of dialysate purification can be improved, and the reduction in the amount of electrolytes in the dialysate that are necessary for the treatment can be suppressed. Furthermore, according to the present embodiment, the amount of substitution fluid used for resupplying electrolytes that are adsorbed by the dialysate purification device 7 can be reduced. Furthermore, the substitution-fluid supply device 8 capable of supplying to the storage device 6 the substitution fluid containing electrolytes that are necessary for blood purification treatment is provided. Therefore, the occurrence of shortage of electrolytes in the dialysate during blood purification treatment can be prevented.

While the embodiments have been described above, the present invention is not limited thereto. The blood purification apparatus only needs to be capable of taking the purification state if a predetermined condition is satisfied after the start of the treatment state. For example, another predetermined condition different from the predetermined condition employed in the above embodiments may be employed (preferably, the condition is defined with reference to a parameter correlating with the concentration of waste matter in the dialysate). Moreover, the substitution-fluid supply device 8 or the waste-matter-concentration measurement device (S) may be omitted. Alternatively, the weighing machine 9 may be omitted (for example, a predetermined amount of substitution fluid may be supplied by controlling the flow rate of the pump Pb). Moreover, a dialysate-concentration-checking device (such as a conductometer) for checking whether or not the composition of the dialysate is appropriate may be provided.

The present invention is applicable to any blood purification apparatus that is capable of switchably taking a treatment state in which dialysate circulating through a dialysate circulation line is allowed to be introduced into a blood purification device without flowing through a dialysate purification device and a purification state in which the dialysate in the dialysate circulation line is allowed to be purified by the dialysate purification device, the apparatus being configured to take the purification state if a predetermined condition is satisfied after the start of the treatment state. Such an apparatus may have additional functions or the like.

REFERENCE SIGNS LIST 1 dialyzer (blood purification device)
2 arterial blood circuit
3 venous blood circuit
4 blood pump
5 venous air-trap chamber
6 storage device
7 dialysate purification device
8 substitution-fluid supply device
9 weighing machine
10 control device
11 drain device
L1 dialysate introduction line
L2 dialysate drain line
L3 flow route
L4 flow route
L5 substitution-fluid supply line
L6 flow route
L7, L8 detour line
S waste-matter-concentration measurement device
P1, P2, Pa, Pb pump
Pc ultrafiltration pump
P duplex pump

The invention claimed is:
1. A blood purification apparatus comprising:
a blood circuit through which blood of a patient is allowed to extracorporeally circulate;
a blood purification device that purifies the blood flowing in the blood circuit;

a storage device capable of storing a predetermined amount of dialysate that is necessary for blood purification treatment;

a control device;

a dialysate circulation line through which the dialysate is allowed to circulate by introducing the dialysate in the storage device into the blood purification device and draining waste liquid from the blood purification device into the storage device; and a dialysate purification device that purifies the dialysate in the dialysate circulation line, wherein a treatment state in which the dialysate circulating through the dialysate circulation line is allowed to be introduced into the blood purification device without flowing through the dialysate purification device and a purification state in which the dialysate in the dialysate circulation line is allowed to be purified by the dialysate purification device are taken switchably, wherein the dialysate is moved through the blood purification device in the purification state by the control device changing movement of the dialysate from the treatment state to the purification state if a predetermined condition is satisfied after a start of the treatment state; and wherein the storage device includes a first storage device and a second storage device in each of which a predetermined amount of dialysate is stored; wherein the dialysate circulation line includes a first circulation-route system through which the dialysate in the first storage device is allowed to circulate via the blood purification device, and a second circulation-route system through which the dialysate in the second storage device is allowed to circulate via the blood purification device; and wherein when one of the first circulation-route system and the second circulation-route system is in the treatment state, and other is in the purification state.

2. The blood purification apparatus according to claim 1, wherein the control device alternates the dialysate between the treatment state and the purification state during blood purification treatment.

3. The blood purification apparatus according to claim 1, further comprising a substitution-fluid supply device capable of supplying substitution fluid containing electrolytes that are necessary for blood purification treatment to the dialysate before the dialysate purified by the dialysate purification device reaches the blood purification device.

4. The blood purification apparatus according to claim 1, further comprising a waste-liquid concentration sensor, and wherein the predetermined condition is defined as an estimated elapsed time that a concentration of waste matter in the dialysate circulating through the dialysate circulation line to reach a predetermined concentration after the start of the treatment state as measured by the waste-liquid concentration sensor.

5. The blood purification apparatus according to claim 1, further comprising a detour line to which the dialysate purification device is provided and that allows the dialysate flowing in the dialysate circulation line to detour, wherein the flow into the detour line is prevented in the treatment state, whereas the dialysate is allowed to flow into the detour line and to be purified by the dialysate purification device in the purification state.

6. The blood purification apparatus according to claim 2, further comprising a substitution-fluid supply device capable of supplying substitution fluid containing electrolytes that are necessary for blood purification treatment to the dialysate before the dialysate purified by the dialysate purification device reaches the blood purification device.

7. The blood purification apparatus according to claim 1, further comprising a waste-matter-concentration measurement device capable of measuring a concentration of waste matter in the dialysate circulating through the dialysate circulation line, wherein the concentration of waste matter is measured by the waste-matter-concentration measurement device to determine when a predetermined concentration is achieved after the start of the treatment state.

8. The blood purification apparatus according to claim 7, further comprising a detour line to which the dialysate purification device is provided and that allows the dialysate flowing in the dialysate circulation line to detour, wherein the flow into the detour line is prevented in the treatment state, whereas the dialysate is allowed to flow into the detour line and to be purified by the dialysate purification device in the purification state.

* * * * *